(12) United States Patent
Itoi

(10) Patent No.: US 9,899,601 B2
(45) Date of Patent: Feb. 20, 2018

(54) MATERIAL FOR ORGANIC ELECTROLUMINESCENT DEVICE AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventor: Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 96 days.

(21) Appl. No.: 15/066,305

(22) Filed: Mar. 10, 2016

(65) Prior Publication Data
US 2016/0359113 A1 Dec. 8, 2016

(30) Foreign Application Priority Data

Jun. 3, 2015 (JP) ................................. 2015-113017

(51) Int. Cl.
*H01L 51/00* (2006.01)
*C07C 211/54* (2006.01)
(Continued)

(52) U.S. Cl.
CPC .......... *H01L 51/006* (2013.01); *C07B 59/001* (2013.01); *C07C 211/54* (2013.01);
(Continued)

(58) Field of Classification Search
None
See application file for complete search history.

(56) References Cited

U.S. PATENT DOCUMENTS 5,840,217 A * 11/1998 Lupo ....................... C07C 13/72
                                                              252/500
6,406,804 B1 * 6/2002 Higashi .................. C09K 11/06
                                                              252/301.16
(Continued)

FOREIGN PATENT DOCUMENTS

JP          2004-315495 A      11/2004
JP          2005-120030 A       5/2005
(Continued)

*Primary Examiner* — Robert S Loewe
(74) *Attorney, Agent, or Firm* — Lewis Roca Rothgerber Christie LLP

(57) ABSTRACT

A material for an organic electroluminescent device having high emission efficiency, represented by Formula 1, and an organic electroluminescent device including the same:

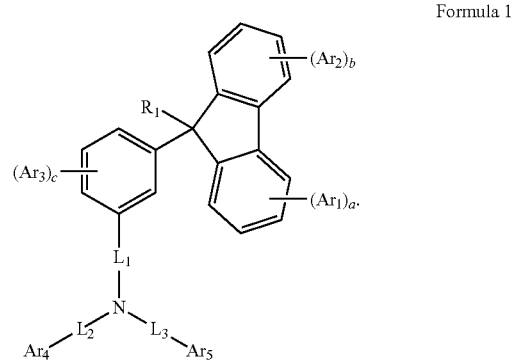

Formula 1

The organic electroluminescent device may include a first electrode, a second electrode facing the first electrode, and one or more organic layers between the first electrode and second electrode. When the material for an organic elec-
(Continued)

troluminescent device is included in at least one of the organic layers, the organic electroluminescent device may achieve high emission efficiency and long lifespan.

10 Claims, 2 Drawing Sheets

(51) Int. Cl.
  *C07C 211/58* (2006.01)
  *C07B 59/00* (2006.01)
  *H01L 51/50* (2006.01)

(52) U.S. Cl.
  CPC ........ *C07C 211/58* (2013.01); *C07C 2603/18* (2017.05); *H01L 51/0052* (2013.01); *H01L 51/0058* (2013.01); *H01L 51/5012* (2013.01); *H01L 51/5056* (2013.01)

(56) References Cited

U.S. PATENT DOCUMENTS

| | | | | |
|---|---|---|---|---|
| 6,822,094 | B2* | 11/2004 | Salbeck | C07C 217/92 544/230 |
| 6,887,392 | B2* | 5/2005 | Ogino | H01L 27/3211 216/2 |
| 7,303,937 | B2* | 12/2007 | Chen | B82Y 10/00 427/427.1 |
| 7,326,474 | B2* | 2/2008 | Kim | C07C 13/72 252/301.16 |
| 7,540,978 | B2* | 6/2009 | Pfeiffer | C09K 11/06 136/263 |
| 7,547,562 | B2* | 6/2009 | Ogino | H01L 27/3211 257/E33.001 |
| 2002/0093283 | A1* | 7/2002 | Seo | H01L 51/5012 313/504 |
| 2004/0110958 | A1* | 6/2004 | Nishiyama | C07C 211/58 546/285 |
| 2005/0189543 | A1* | 9/2005 | Yamazaki | H01L 29/78621 257/72 |
| 2006/0040132 | A1* | 2/2006 | Liao | H01L 51/5036 428/690 |
| 2006/0063027 | A1* | 3/2006 | Vestweber | C07C 13/72 428/690 |
| 2006/0180812 | A1* | 8/2006 | Sakata | H01L 51/5012 257/40 |
| 2007/0003785 | A1* | 1/2007 | Slusarek | H01L 51/006 428/690 |
| 2007/0116984 | A1* | 5/2007 | Park | C07D 221/20 428/690 |
| 2007/0149784 | A1* | 6/2007 | Murata | C07D 273/00 548/143 |
| 2007/0215867 | A1* | 9/2007 | Kawakami | C07C 211/61 257/40 |
| 2008/0122345 | A1* | 5/2008 | Sakata | C07C 211/61 313/504 |
| 2008/0124572 | A1* | 5/2008 | Mizuki | C07C 211/54 428/690 |
| 2008/0199726 | A1* | 8/2008 | Schafer | C07D 239/26 428/690 |
| 2008/0206598 | A1* | 8/2008 | Ohsawa | H01L 51/006 428/690 |
| 2009/0160323 | A1* | 6/2009 | Nomura | C07D 209/86 313/504 |
| 2010/0301744 | A1* | 12/2010 | Osaka | C07C 211/54 313/504 |
| 2011/0037027 | A1* | 2/2011 | Stoessel | C07C 13/567 252/301.16 |
| 2011/0220881 | A1* | 9/2011 | Yokoyama | C07F 7/0812 257/40 |
| 2012/0161107 | A1* | 6/2012 | Yokoyama | C07D 213/22 257/40 |

FOREIGN PATENT DOCUMENTS

| | | |
|---|---|---|
| JP | 2009-29726 A | 2/2009 |
| JP | 2009-267255 A | 11/2009 |
| JP | 2011-521894 A | 7/2011 |
| JP | 2012-46478 A | 3/2012 |
| JP | 2013-67641 A | 4/2013 |
| KR | 10-1211091 B1 | 12/2012 |
| WO | WO 2010/074440 A2 | 7/2010 |
| WO | WO 2010/137601 A1 | 12/2010 |
| WO | WO-2013135352 A1 * | 9/2013 ........ H01L 51/006 |

* cited by examiner

MATERIAL FOR ORGANIC ELECTROLUMINESCENT DEVICE AND ORGANIC ELECTROLUMINESCENT DEVICE INCLUDING THE SAME

CROSS-REFERENCE TO RELATED APPLICATION

This patent application claims priority and to the benefit of Japanese Patent Application No. 2015-113017, filed on Jun. 3, 2015, the entire content of which is incorporated herein by reference.

BACKGROUND

One or more aspects of embodiments of the present disclosure are related to a material for an organic electroluminescent device and an organic electroluminescent device including the same, and more particularly, to a hole transport material for an organic electroluminescent device having high emission efficiency and a long lifespan, and an organic electroluminescent device including the same.

Organic electroluminescent (EL) image displays have been actively developed in recent years. Unlike liquid crystal displays and the like, organic EL displays are so-called "self-luminescent displays", in which holes and electrons are respectively injected from anodes and cathodes into an emission layer, where they recombine and cause light to be emitted from a luminescent organic material in the emission layer, thereby displaying images.

An example organic EL device may include an anode, a hole transport layer on the anode, an emission layer on the hole transport layer, an electron transport layer on the emission layer, and a cathode on the electron transport layer. Holes from the anode may be injected via the hole transport layer into the emission layer. Electrons from the cathode may be concurrently (e.g., simultaneously) injected via the electron transport layer into the emission layer. The holes and the electrons injected into the emission layer may recombine to generate excitons within the emission layer. The organic EL device may emit light generated by radiative decay of the excitons. Organic EL devices are not limited to the above-described configuration, but may be produced in one or more suitable forms.

Display applications require organic EL devices having high efficiencies. However, organic EL devices in the blue light-emitting region require high driving voltages, and may therefore suffer from low emission efficiencies compared to organic EL devices in the green and red light-emitting regions. Previously attempted strategies for achieving organic EL devices with high efficiencies include normalization and stabilization of the hole transport layer and enhancement of durability.

Various organic EL devices in the related art have used aromatic amine-based compounds as hole transport materials in the hole transport layer. However, the emission efficiencies and lifespans of these devices have been limited. For example, an amine derivative having a substituent aryl group or heteroaryl group has been suggested as an material that may extend the lifespan of organic EL devices. However, organic EL device employing these amine derivative materials have not exhibited sufficient emission efficiencies and lifespans. Thus organic EL devices having improved lifespans are still highly desired.

Furthermore, although a compound in which fluorene is bound to the nitrogen atom of a monoamine through a phenylene linker is known to exhibit high hole transport-ability, there still remains a need for compounds with sufficiently high emission efficiencies and long lifespans.

SUMMARY

One or more aspects of embodiments of the present disclosure are directed toward a material for an organic electroluminescent device having a high emission efficiency, and an organic electroluminescent device including the same.

One or more aspects of embodiments of the present disclosure are directed toward a material for an organic electroluminescent device that emits light in the green to blue regions and has high emission efficiency and a long lifespan, as well as an organic electroluminescent device including the same, wherein the material is used in at least one of the laminated layers between an emission layer and an anode.

One or more embodiments of the present disclosure provide a material for an organic electroluminescent device represented by Formula 1:

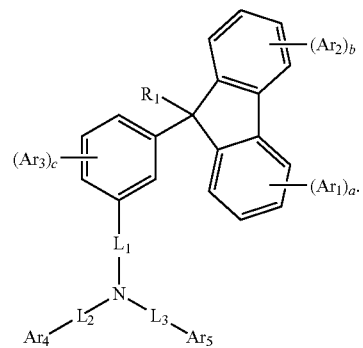

Formula 1

In Formula 1, $R_1$ may be selected from a substituted or unsubstituted aryl group having 6 to 10 carbon atoms for forming a ring and an alkyl group having 1 to 20 carbon atoms, $Ar_1$ to $Ar_5$ may each independently be selected from a substituted or unsubstituted aryl group having 6 to 30 carbon atoms for forming a ring, a substituted or unsubstituted heteroaryl group having 5 to 30 carbon atoms for forming a ring, an alkyl group having 1 to 20 carbon atoms, a silyl group, a halogen atom, deuterium, and hydrogen, at least one selected from $Ar_4$ and $Ar_5$ may be a substituted or unsubstituted naphthyl group, $L_1$ to $L_3$ may each independently be selected from a single bond and a substituted or unsubstituted arylene group having 6 to 12 carbon atoms for forming a ring, and a to c may each independently be an integer selected from 0 to 4.

In one embodiment, the material for an organic electroluminescent device may improve the emission efficiency and lifespan of the organic electroluminescent device by introducing (e.g., coupling) a fluorenyl group and/or a naphthyl group to an amine.

In one embodiment, $R_1$ may be selected from a substituted or unsubstituted phenyl group and a substituted or unsubstituted naphthyl group.

In one embodiment, when $R_1$ is selected from a substituted or unsubstituted phenyl group and a substituted or unsubstituted naphthyl group, the material for an organic electroluminescent device may improve the lifespan of an organic electroluminescent device.

In one embodiment, at least one selected from $L_1$ to $L_3$ may be a phenylene group.

In one embodiment, when at least one selected from $L_1$ to $L_3$ is a phenylene group, the material for an organic electroluminescent device may improve the lifespan of an organic electroluminescent device.

One or more embodiments of the present disclosure provide an organic electroluminescent device including the material for an organic electroluminescent device in at least one layer.

In one embodiment, the organic electroluminescent device may include a first electrode, a second electrode facing the first electrode, and one or more organic layers between the first electrode and the second electrode, wherein at least one selected from the one or more organic layers includes the material for an organic electroluminescent device.

In one embodiment, when the material for an organic electroluminescent device is included in at least one layer, the organic electroluminescent device may achieve high emission efficiency and long lifespan.

One or more embodiments of the present disclosure provide an organic electroluminescent device including the material for an organic electroluminescent device in at least one laminated layer between an emission layer and an anode.

In one embodiment, the organic electroluminescent device may include an emission layer between the first electrode and the second electrode, and the material for an organic electroluminescent device may be in at least one of the one or more organic layers between the first electrode and the emission layer.

In one embodiment, when the material for an organic electroluminescent device is included in at least one laminated layer between the emission layer and the anode, the organic electroluminescent device may achieve high emission efficiency and long lifespan.

In one embodiment, the organic layer including the material for an organic electroluminescent device may be at least one selected from a hole injection layer and a hole transport layer.

In one embodiment, the organic electroluminescent device may achieve high emission efficiency and long lifespan by including the material for an organic electroluminescent device in at least one selected from the hole injection layer and the hole transport layer.

BRIEF DESCRIPTION OF THE DRAWINGS

The accompanying drawings are included to enable further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
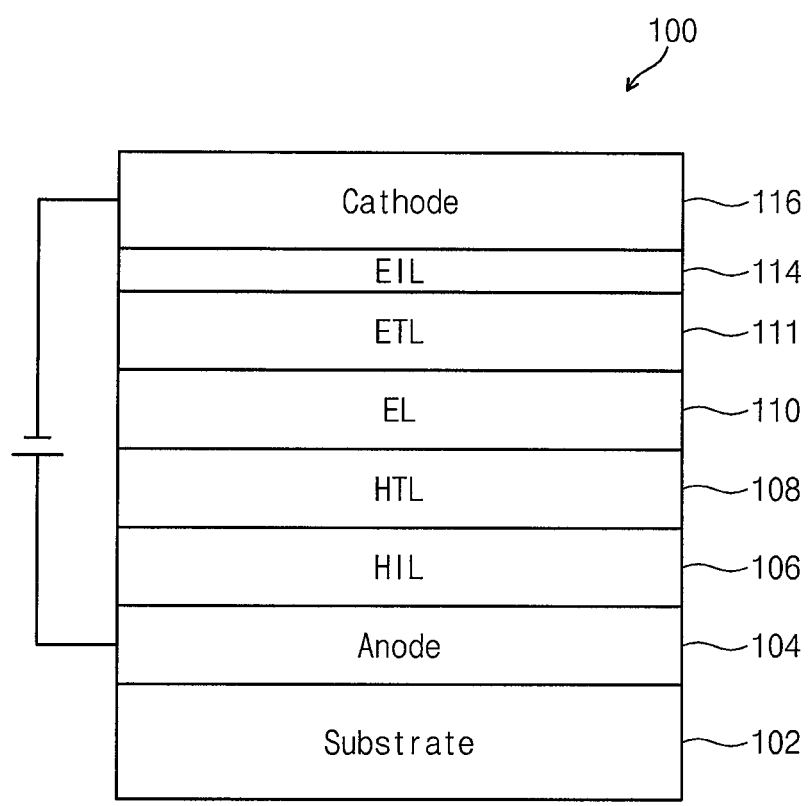
FIG. 1 is a schematic diagram showing an organic electroluminescent device according to an embodiment of the present disclosure.

When a fluorenyl group and a naphthyl group having high charge resistance are introduced (e.g., coupled) to an amine moiety in an organic electroluminescent device according to an embodiment of the present disclosure, the organic electroluminescent device may achieve long lifespan. Also, when the fluorenyl group is coupled to the amine via an m-phenylene linker, the organic electroluminescent device may exhibit high efficiency.

Hereinafter, a material for an organic electroluminescent device according to an embodiment of the present disclosure and an organic electroluminescent device including the material will be described in more detail with reference to the accompanying drawings. The material for an organic electroluminescent device according to an embodiment of the present disclosure and the organic electroluminescent device including the material may, however, be embodied in different forms, and should not be construed as being limited to the example embodiments set forth herein. In the drawings, like reference numerals refer to like elements or elements having like functions throughout, and repeated explanation thereof will not be provided.

In the drawings, the thicknesses of layers, films, panels, regions, etc., may be exaggerated for clarity. It will be understood that when an element such as a layer, film, region, or substrate is referred to as being "on" another element, it can be directly on the other element or intervening element(s) may also be present. In contrast, when an element is referred to as being "directly on" another element, no intervening elements are present.

One or more aspects of embodiments of the present disclosure provide a material for an organic electroluminescent device that is an amine compound represented by the following Formula 1:

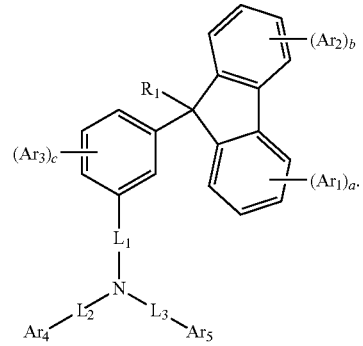

Formula 1

In Formula 1, $R_1$ may be selected from a substituted or unsubstituted aryl group having 6 to 10 carbon atoms for forming a ring and an alkyl group having 1 to 20 carbon atoms. $Ar_1$ to $Ar_5$ may each independently be selected from a substituted or unsubstituted aryl group having 6 to 30 carbon atoms for forming a ring, a substituted or unsubstituted heteroaryl group having 5 to 30 carbon atoms for forming a ring, an alkyl group having 1 to 20 carbon atoms, a silyl group, a halogen atom, deuterium, and hydrogen, and at least one selected from $Ar_4$ and $Ar_5$ may be a substituted or unsubstituted naphthyl group. $L_1$ to $L_3$ may each independently be selected from a single-bond and a substituted or unsubstituted arylene group having 6 to 12 carbon atoms for forming a ring. a to c may each independently be an integer selected from 0 to 4. As used herein, the term "atoms for forming a ring" may refer to "ring-forming atoms".

In one embodiment, in Formula 1, $R_1$ is an aryl group having 6 to 10 carbon atoms for forming a ring. In one embodiment, $R_1$ is selected from a phenyl group and a naphthyl group, but embodiments of the present disclosure are not limited thereto.

In Formula 1, non-limiting examples of the alkyl group having 1 to 20 carbon atoms for forming a ring used in $R_1$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc., but embodiments of the present disclosure are not limited thereto.

In Formula 1, non-limiting examples of the aryl group having 6 to 30 carbon atoms for forming a ring used in $Ar_1$ to $Ar_5$ may include a phenyl group, a naphthyl group, an anthracenyl group, a phenanthryl group, a biphenyl group, a terphenyl group, a quaterphenyl group, a fluorenyl group, a triphenylene group, a biphenylene group, a pyrenyl group, a benzofluoranthenyl group, a chrysenyl group, a phenylnaphthyl group, a naphthylphenyl group, etc., and in some embodiments, a phenyl group, a naphthyl group, and a biphenyl group. However, embodiments of the aryl group having 6 to 30 carbon atoms for forming a ring used in $Ar_1$ to $Ar_5$ are not limited thereto.

In some embodiments, non-limiting examples of the heteroaryl group having 5 to 30 carbon atoms for forming a ring used in $Ar_1$ to $Ar_5$ may include a pyridyl group, a quinolyl group, an isoquinolyl group, a benzofuryl group, a benzothienyl group, an indolyl group, a benzoxazolyl group, a benzothiazolyl group, a quinoxalyl group, a benzimidazolyl group, a dibenzofuryl group, a dibenzothienyl group, a carbazolyl group, etc., but embodiments of the present disclosure are not limited thereto.

Non-limiting examples of the alkyl group having 1 to 20 carbon atoms used in $Ar_1$ to $Ar_5$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, an 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc., but embodiments of the present disclosure are not limited thereto.

Non-limiting examples of the silyl group used in $Ar_1$ to $Ar_5$ may include a trialkylsilyl group, a triarylsilyl group, a monoalkyldiarylsilyl group, and a dialkylmonoarylsilyl group (such as a trimethylsilyl group and/or a triphenylsilyl group).

Non-limiting examples of the halogen atom used in $Ar_1$ to $Ar_5$ may include fluorine (F), chlorine (Cl), bromine (Br), etc.

In Formula 1, at least one selected from $Ar_4$ and $Ar_5$ may be a substituted or unsubstituted naphthyl group.

In Formula 1, when $R_1$ and $Ar_1$ to $Ar_5$ are a substituted group, non-limiting examples of the substituent may include an alkyl group such as a methyl group, an ethyl group, a propyl group, a pentyl group, and a hexyl group, and an aryl group such as a phenyl group, a biphenyl group, and a naphthyl group. In some embodiments, $R_1$ and $Ar_1$ to $Ar_5$ may each have a plurality of substituent groups. The substituent groups may be linked (e.g., coupled) to each other to form a saturated or unsaturated ring.

In Formula 1, non-limiting examples of the arylene group having 6 to 12 carbon atoms for forming a ring used in $L_1$ to $L_3$ may include a phenylene group, a biphenylene group, a naphthylene group, etc., but embodiments of the present disclosure are not limited thereto. In some embodiments, at least one selected from $L_1$ to $L_3$ may be an arylene group, and in some embodiments, at least one selected from $L_1$ to $L_3$ may be a phenylene group.

The amine compound represented by Formula 1, which is a material for an organic electroluminescent device according to an embodiment of the present disclosure, may achieve long lifespan and be resistant to degradation due to the combination of the amine moiety having favorable hole transporting properties with a fluorenyl group and a naphthyl group having high charge resistance.

When the amine compound is substituted with (e.g., coupled to) a fluorenyl group through an m-phenylene linker, the molecular symmetry of the material may be destroyed and the amorphous nature of the compound may be enhanced, thereby improving the emission efficiency of the material.

The material for an organic electroluminescent device according to an embodiment of the present disclosure may be further represented by, for example, at least one selected from Compounds 1 to 60 below. However, embodiments of the present disclosure are not limited thereto.
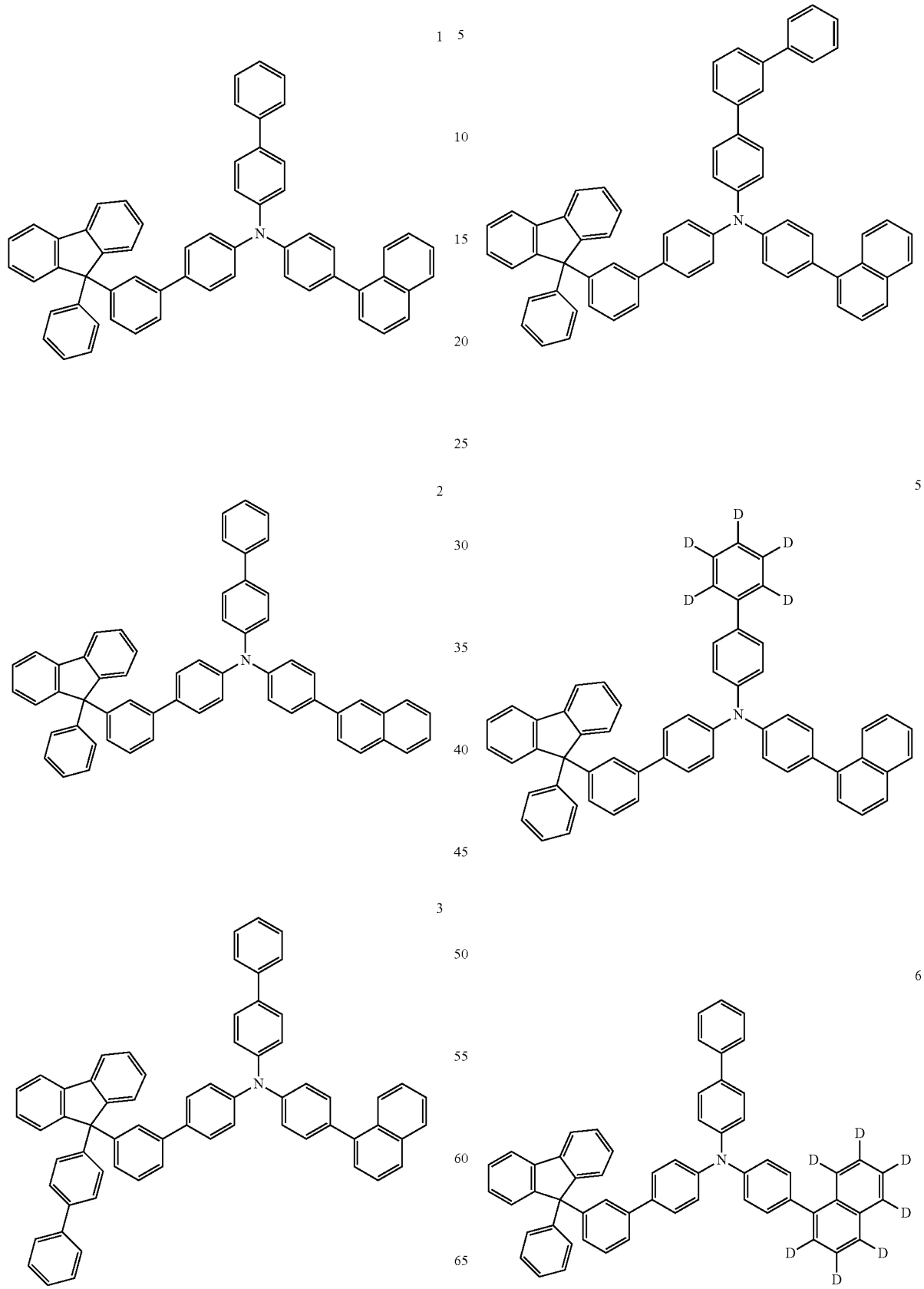

7
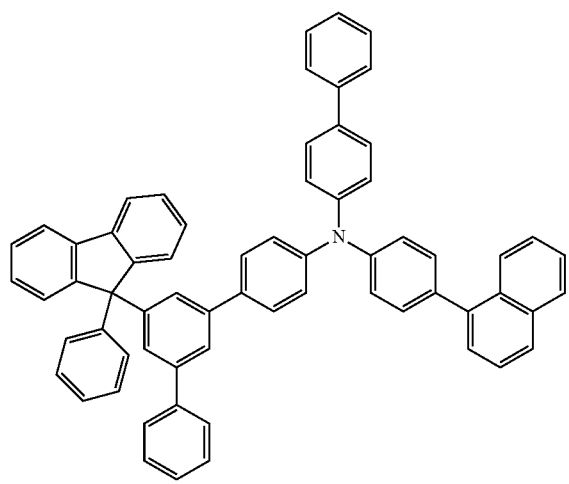
8
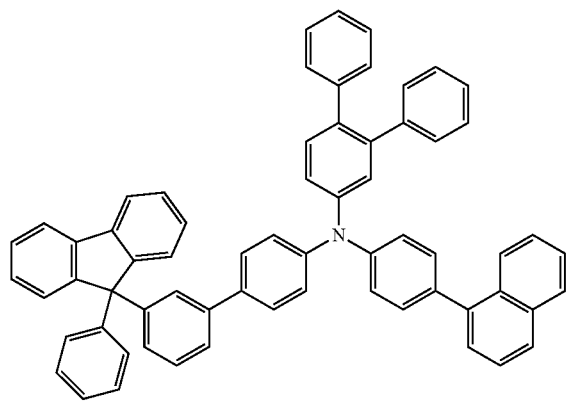
9
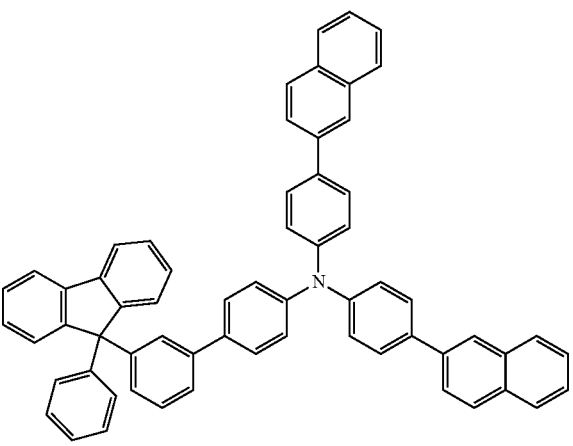
10
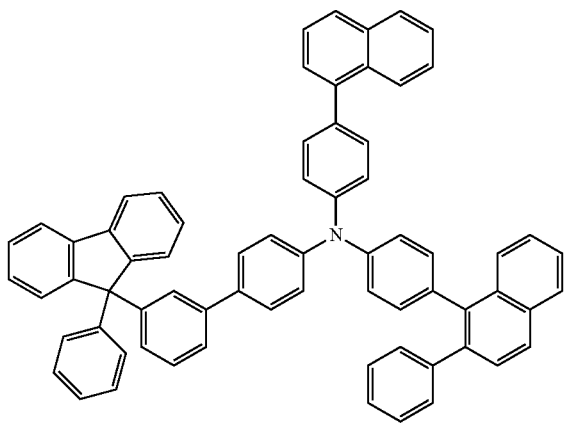
11
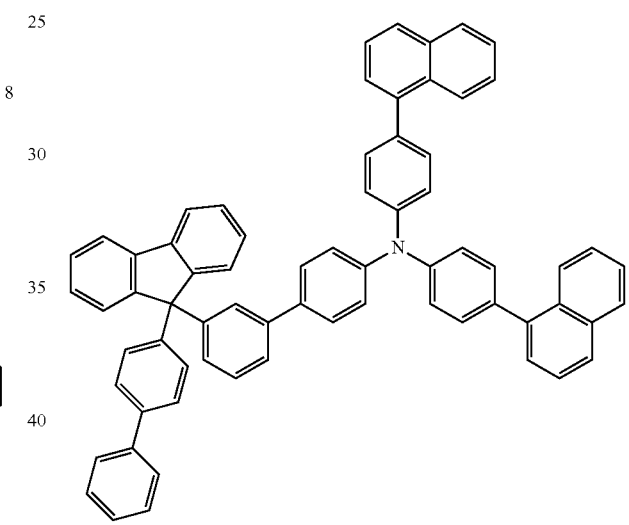
12

13
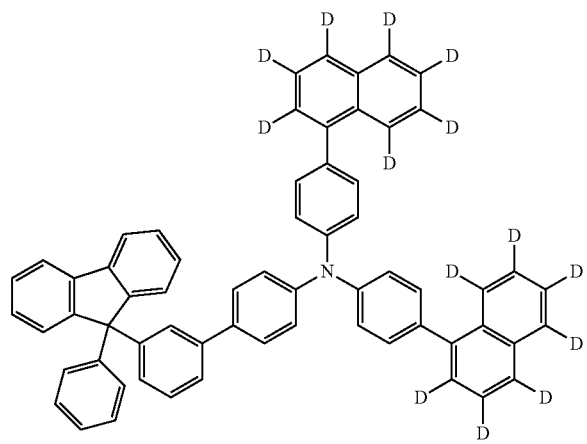
14
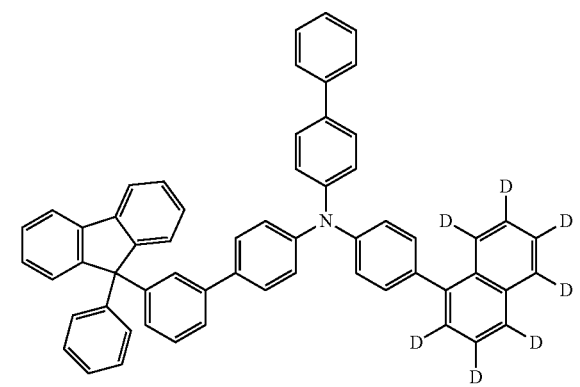
15
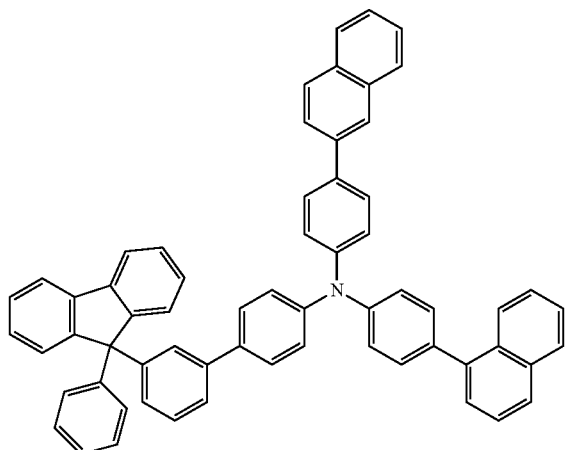
16
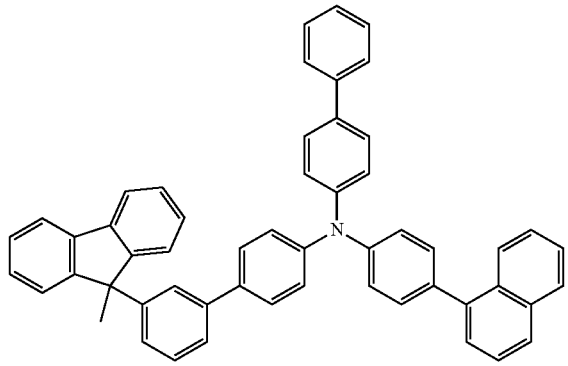
17
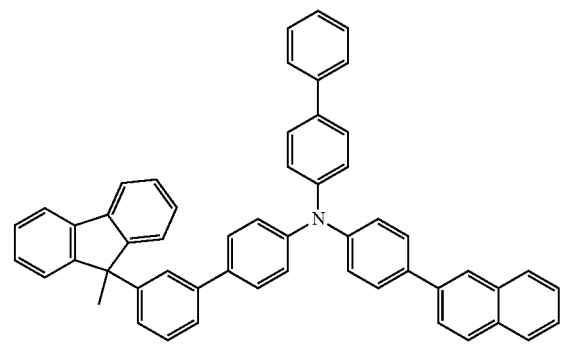
18
19
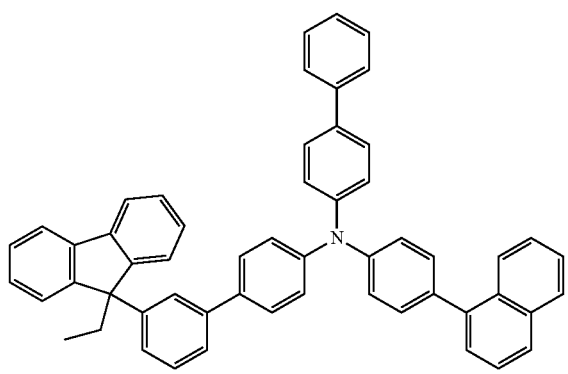

20
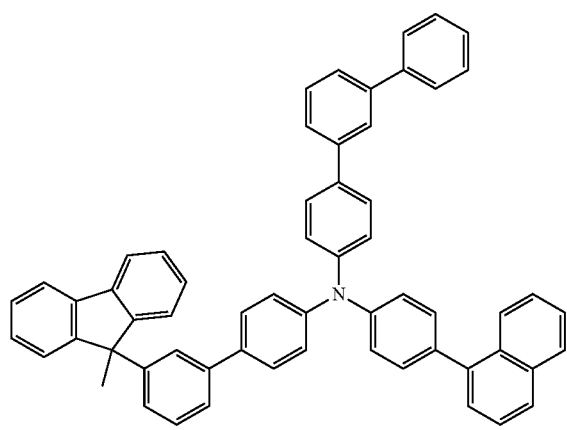
21
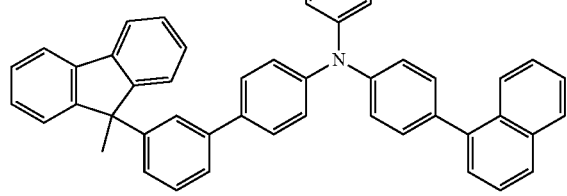
22
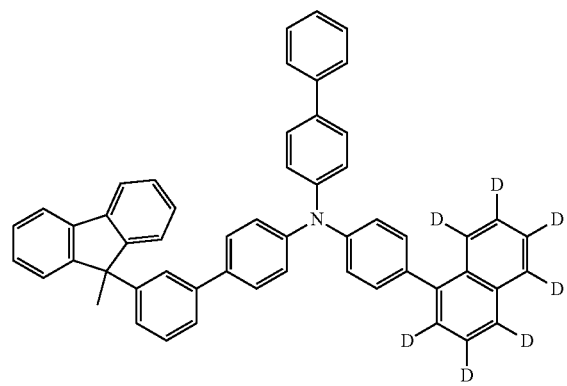
23
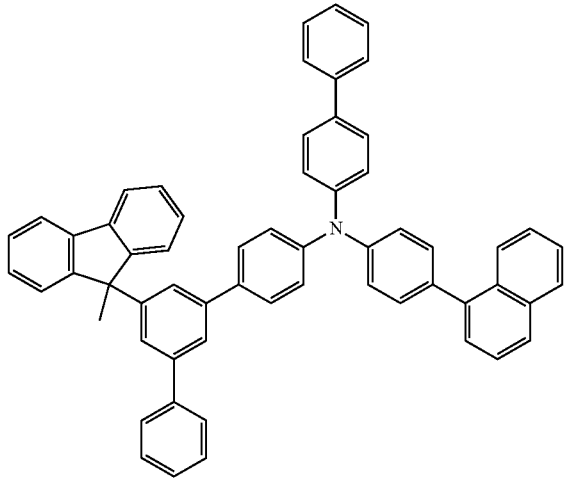
24
25
26
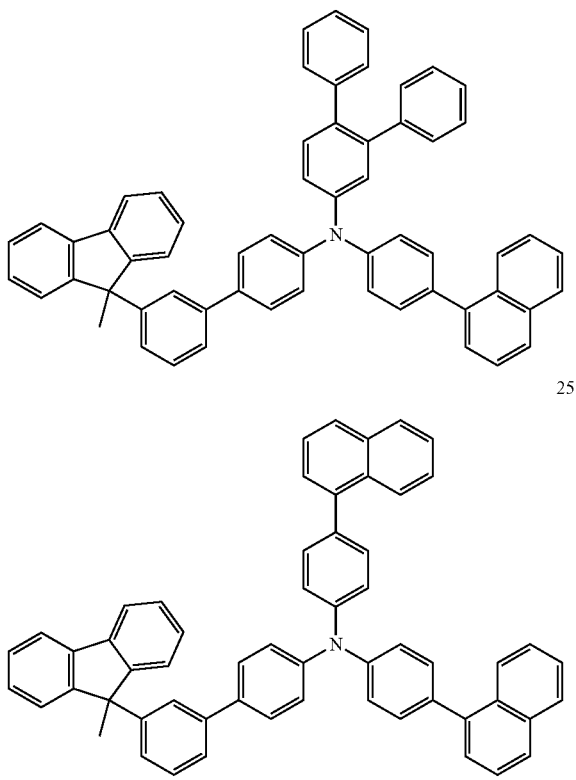

27
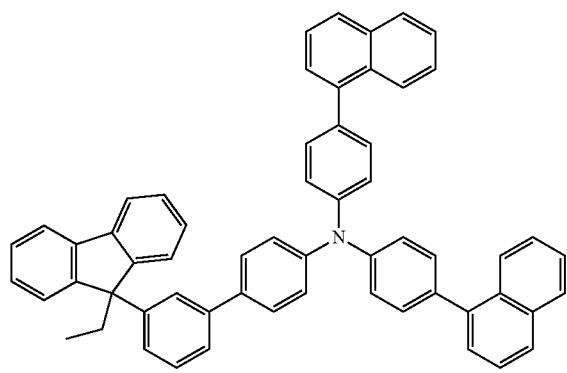
28
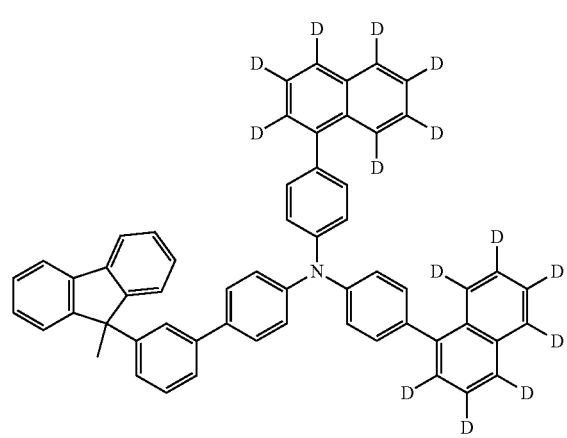
29
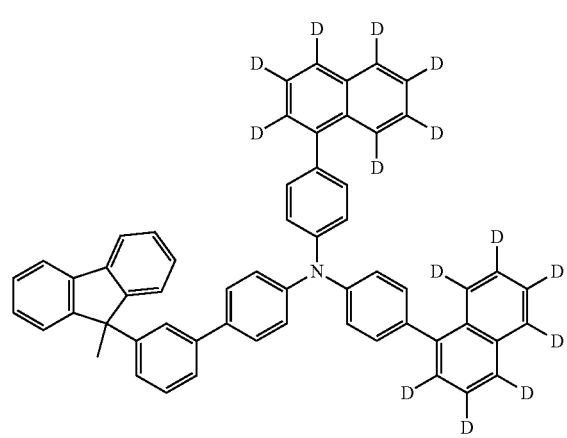
30
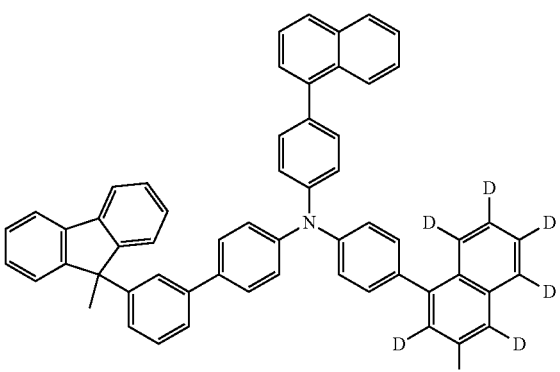
31
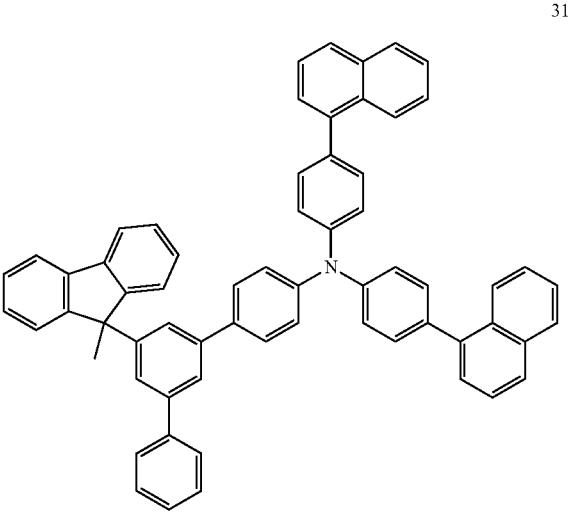
32
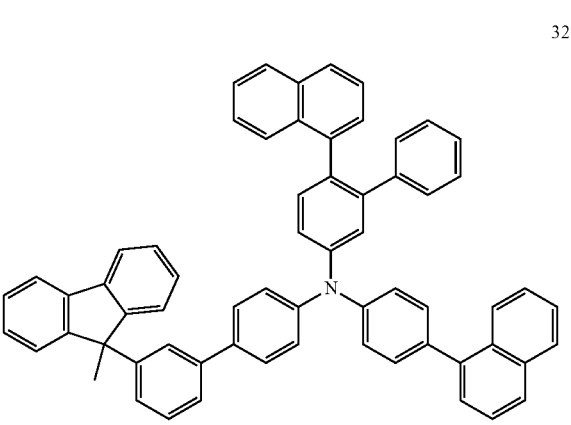

33
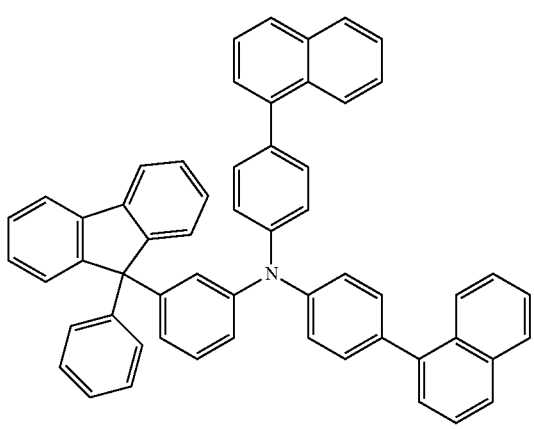
34
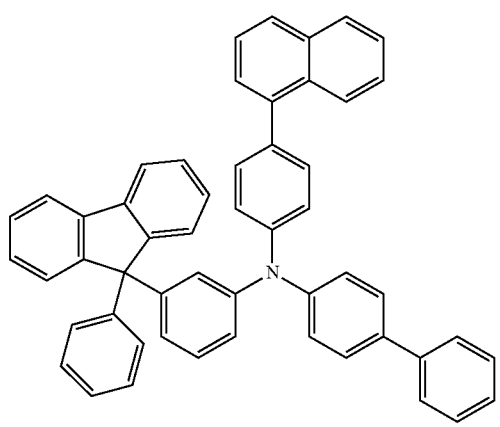
35
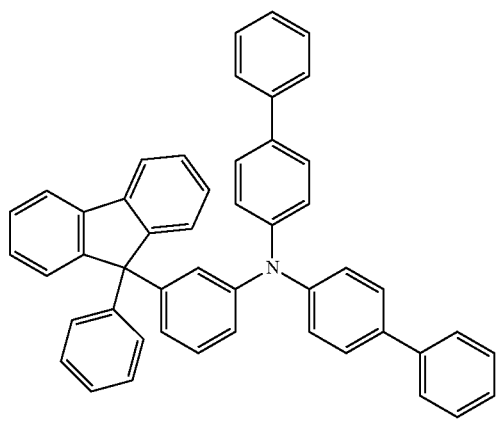
36
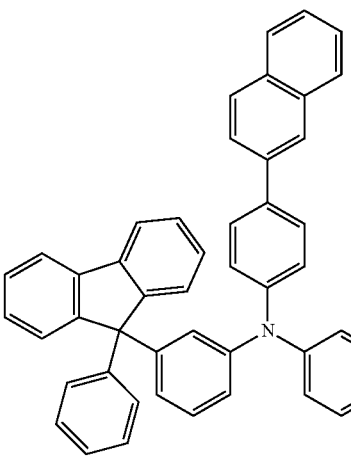
37
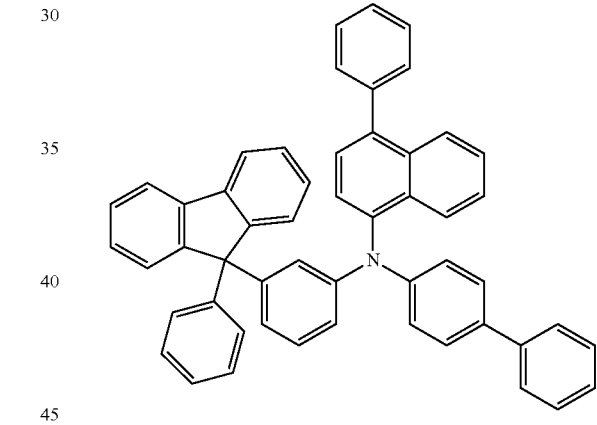
38
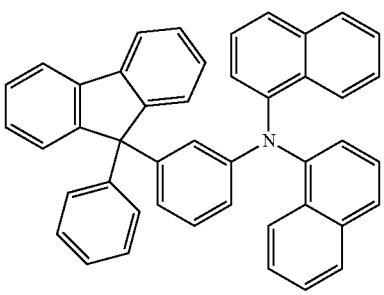

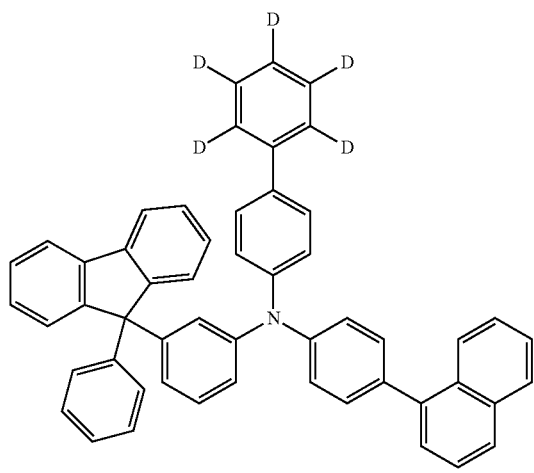
39
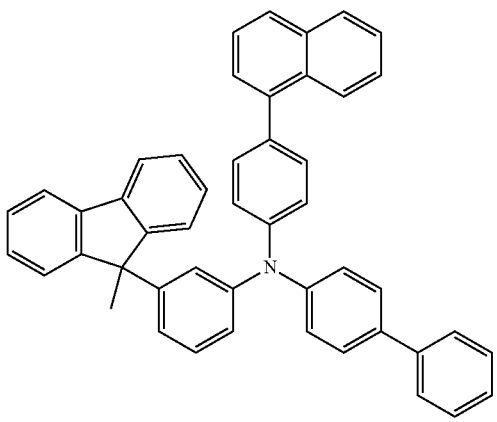
42
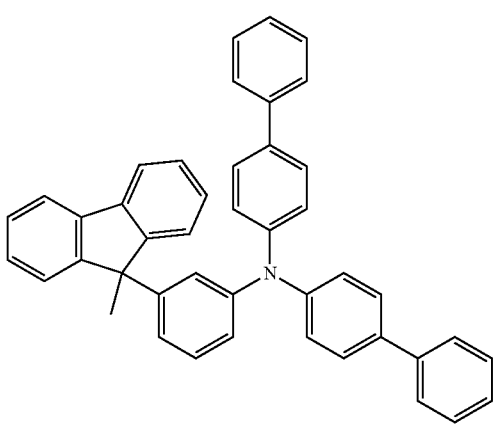
43
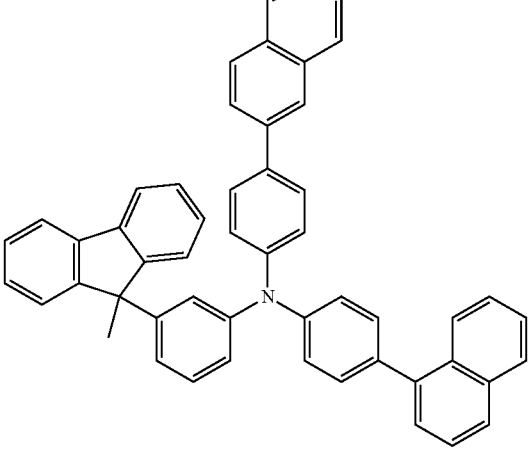
44

45
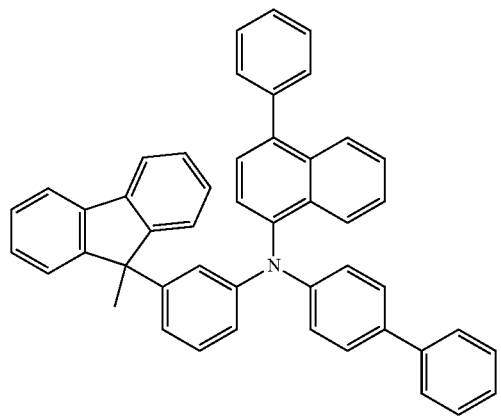
46
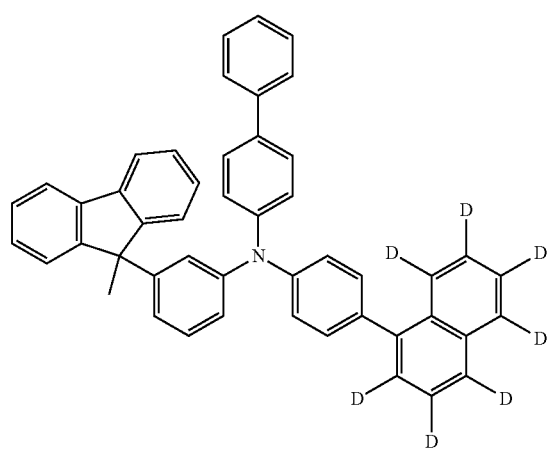
48
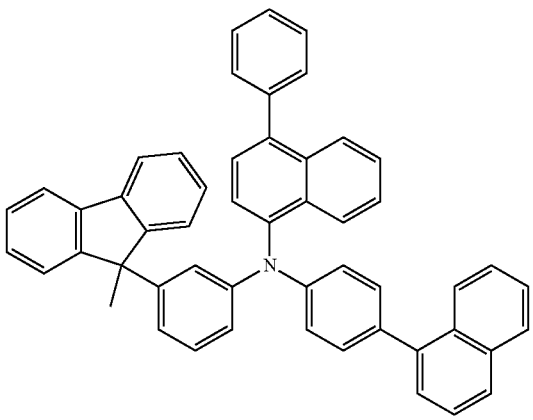
49
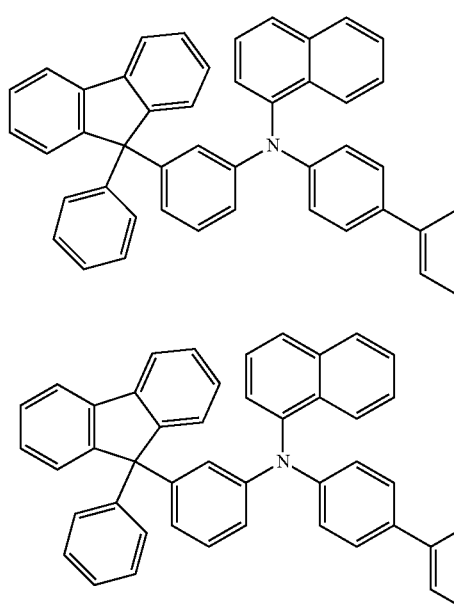
50
51
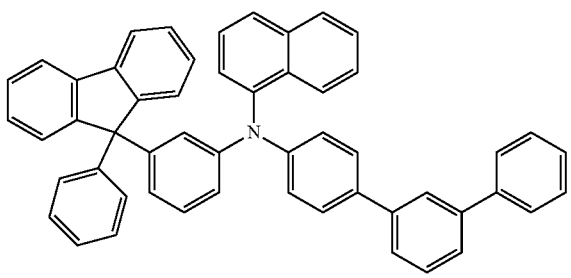
47
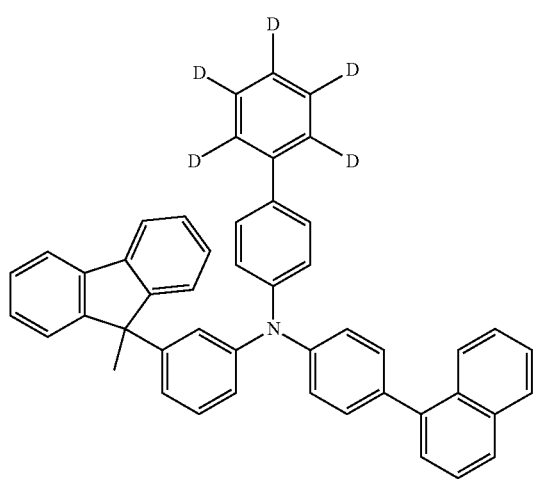
52
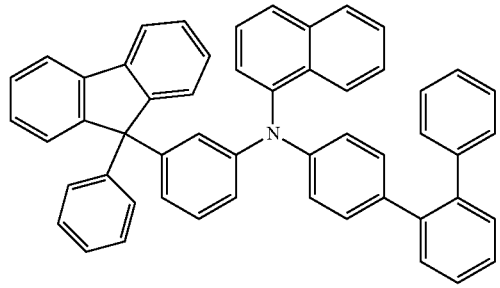

53

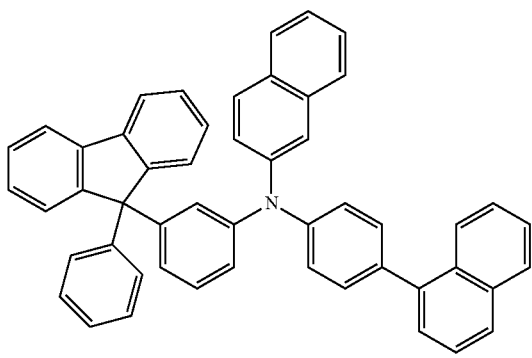

54

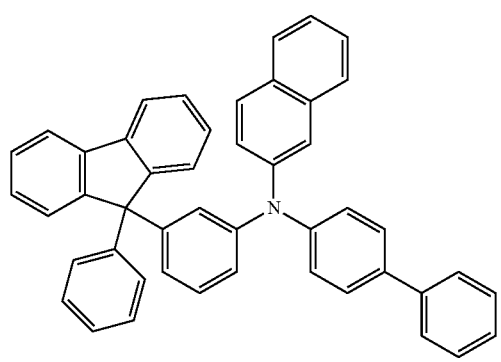

55

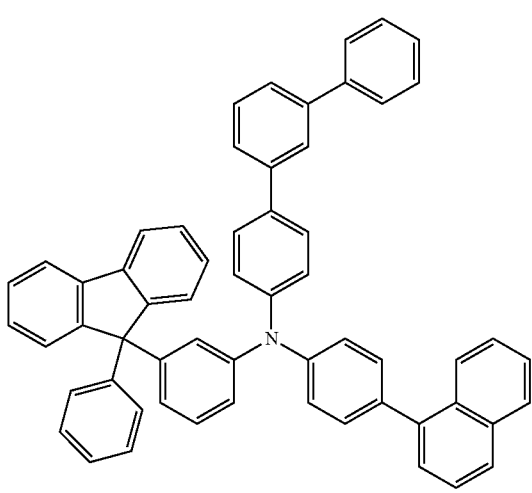

56

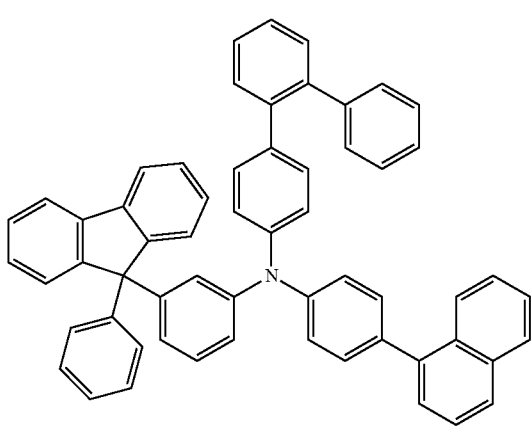

57

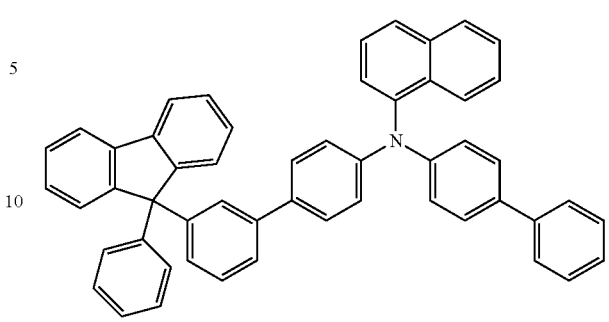

58

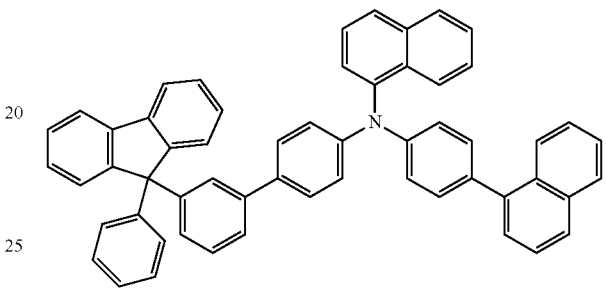

59

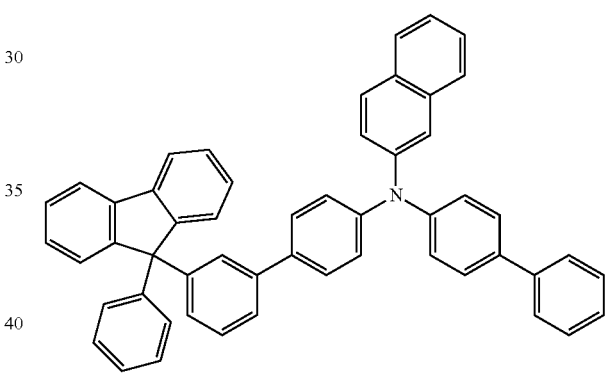

60

The material for an organic electroluminescent device according to an embodiment of the present disclosure may be included in at least one layer selected from a plurality of organic layers constituting the organic electroluminescent device. In particular, the material may be included in at least one laminated layer between an emission layer and an anode of the organic electroluminescent device.

As described above, the material for an organic electroluminescent device according to an embodiment of the present disclosure may achieve long lifespan and be resistant to degradation when a fluorenyl group and a naphthyl group having high charge resistance are introduced (e.g., coupled) to an amine moiety. In some embodiments, when the fluorenyl group is linked (e.g., coupled) to the amine moiety via an m-phenylene linker, the molecular symmetry of the material may be destroyed and the amorphous nature of the compound may be enhanced, thereby improving the emission efficiency of the material.

Organic Electroluminescent Device

An organic electroluminescent device including a material for an organic electroluminescent device according to an embodiment of the present disclosure will be described in more detail. FIG. 1 is a schematic diagram showing an organic electroluminescent device 100 according to an embodiment of the present disclosure. The organic electroluminescent device 100 may include, for example, a substrate 102, an anode 104, a hole injection layer 106, a hole transport layer 108, an emission layer 110, an electron transport layer 111, an electron injection layer 114, and a cathode 116. In one embodiment, the material for an organic electroluminescent device according to an embodiment of the present disclosure may be used in at least one laminated layer between the emission layer and the anode.

An example embodiment will be described in which the material for an organic electroluminescent device according to an embodiment of the present disclosure is used in the hole transport layer 108.

The substrate 102 may be, for example, a transparent glass substrate, a semiconductor substrate formed using silicone, or a flexible substrate (such as resin).

The anode 104 may be on the substrate 102, and may include indium tin oxide (In$_2$O$_3$—SnO$_2$: ITO), indium zinc oxide (In$_2$O$_3$—ZnO), etc.

The hole injection layer (HIL) 106 may be formed on the anode 104 such that the hole injection layer (HIL) has a thickness of about 10 nm to about 150 nm, and may include a suitable material available in the related art. Non-limiting examples of the material may include triphenylamine-containing polyether ketone (TPAPEK), 4-isopropyl-4'-methyl diphenyliodonium tetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound (such as copper phthalocyanine), 4,4',4''-tris(3-methylphenylamino)triphenylamine (m-MTDATA), N,N'-di(1-naphthyl)-N,N'-diphenyl benzidine (NPB), 4,4',4''-tris{N, N-diamino}triphenyl amine (TDATA), 4,4',4''-tris(N,N-2-naphthylphenylamino)triphenylamine (2-TNATA), polyaniline/dodecyl benzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), etc.

The hole transport layer (HTL) 108 may be formed on the hole injection layer (HIL) 106 using the material for an organic electroluminescent device according to an embodiment of the present disclosure, such that the hole transport layer (HTL) has a thickness of about 3 nm to about 100 nm. The hole transport layer (HTL) 108 including the material for an organic electroluminescent device according to an embodiment of the present disclosure may be formed through, for example, vacuum deposition.

The emission layer (EL) 110 may be formed on the hole transport layer (HTL) 108 using a suitable host material available in the related art, such that the emission layer (EL) 110 has a thickness of about 10 nm to about 60 nm. A derivative of a condensed polycyclic aromatic group may be included as a host material in the emission layer (EL) 110.

In some embodiments, the material may be selected from an anthracene derivative, a pyrene derivative, a fluoranthene derivative, a chrysene derivative, a benzoanthracene derivative, and a triphenylene derivative. In some embodiments, the emission layer (EL) 110 may contain an anthracene derivative and/or a pyrene derivative. The anthracene derivative used in the emission layer (EL) 110 may include a compound represented by Formula 2:

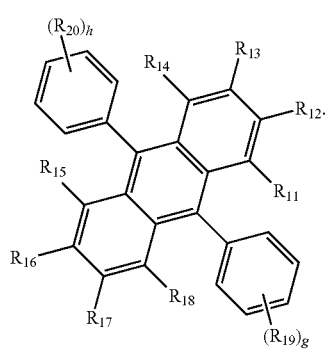

Formula 2

In Formula 2, $R_{11}$ to $R_{20}$ may each independently be selected from a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a silyl group, a halogen atom, hydrogen, and deuterium. In some embodiments, g and h may each independently be an integer selected from 0 to 5. Additionally, a plurality of adjacent $R_{11}$ to $R_{20}$ groups may be linked to each other to form a saturated or unsaturated ring.

Non-limiting examples of the substituted or unsubstituted heteroaryl group having 1 to 30 carbon atoms for forming a ring used in $R_{11}$ to $R_{20}$ may include a benzothiazolyl group, a thiophenyl group, a thienothiophenyl group, a thienothienothiophenyl group, a benzothiophenyl group, a benzofuryl group, a dibenzothiophenyl group, a dibenzofuryl group, an N-arylcarbazolyl group, an N-heteroarylcarbazolyl group, an N-alkylcarbazolyl group, a phenoxazyl group, a phenothiazyl group, a pyridyl group, a pyrimidyl group, a triazyl group, a quinolinyl group, a quinoxalyl group, etc.

Non-limiting examples of a substituted or unsubstituted heteroaryl group having 1 to 30 carbon atoms for forming a ring used in $R_{11}$ to $R_{20}$ may include a benzothiazolyl group, a thiophenyl group, a thienothiophenyl group, a thienothienothiophenyl group, a benzothiophenyl group, a benzofuryl group, a dibenzothiophenyl group, a dibenzofuryl group, an N-arylcarbazolyl group, an N-heteroaryl carbazolyl group, an N-alkyl carbazolyl group, a phenoxazyl group, a phenothiazyl group, a pyridyl group, a pyrimidyl group, a triazyl group, a quinolinyl group, a quinoxalyl group, etc.

Non-limiting examples of the alkyl group having 1 to 15 carbon atoms used in $R_{11}$ to $R_{20}$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc.

The anthracene derivative used in the emission layer (EL) 110 of the organic electroluminescent device according to an embodiment of the present disclosure may be represented by at least one selected from Compounds a-1 to a-12. However, embodiments of the anthracene derivative are not limited thereto.

a-1

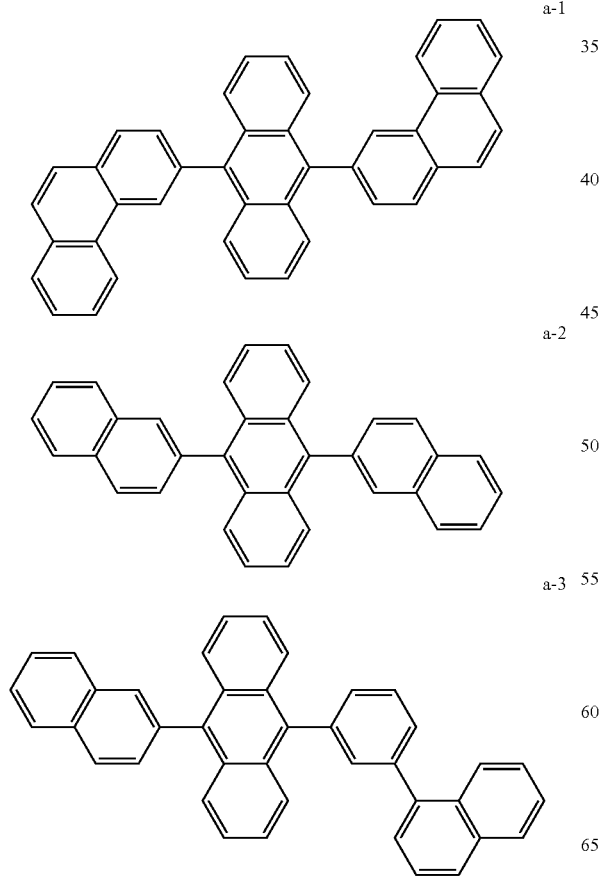

a-2 a-3

-continued a-4

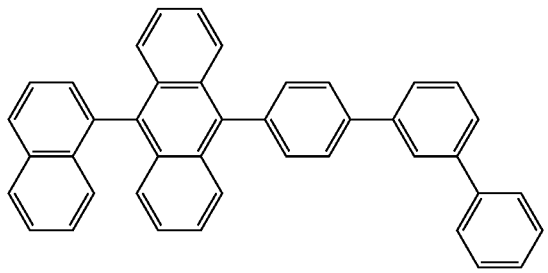

a-5

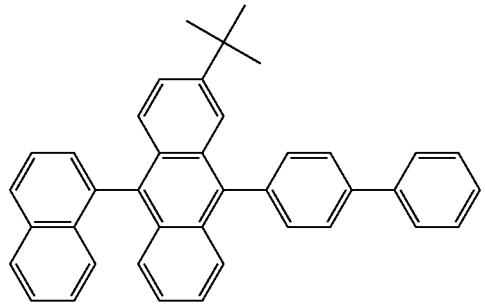

a-6

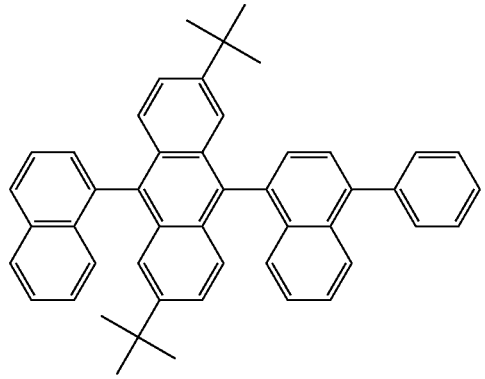

a-7

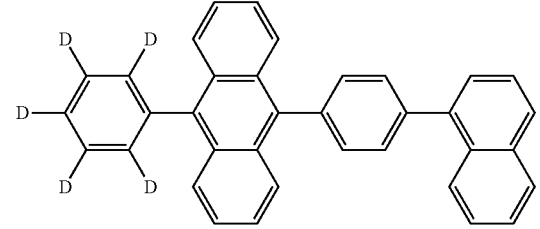

a-8

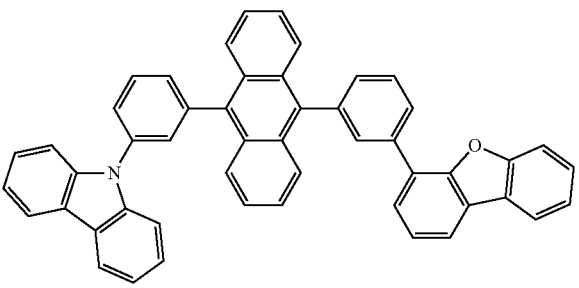

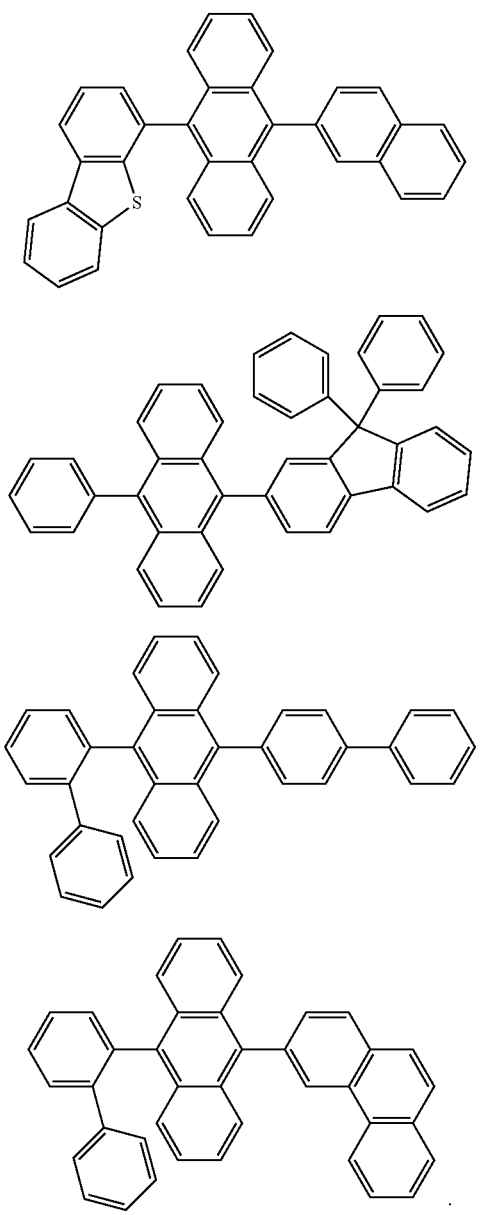

a-9 a-10 a-11 a-12

The emission layer (EL) 110 may include a dopant material such as a styryl derivative (for example, 1,4-bis[2-(3-N-ethylcarbazoryl)vinyl]benzene (BCzVB), 4-(di-p-tolylamino)-4'-[(di-p-tolylamino)styryl]stilbene (DPAVB) and/or N-(4-((E)-2-(6-((E)-4-(diphenylamino)styryl) naphthalene-2-yl)vinyl)phenyl-N-phenylbenzenamine (N-BDAVBi)), perylene and derivatives thereof (for example, 2,5,8,11-tetra-t-butylperylene (TBP)), pyrene and derivatives thereof (for example, 1,1-dipyrene, 1,4-dipyrenylbenzene, 1,4-bis(N,N-diphenylamino)pyrene), etc., but embodiments of the present disclosure are not limited thereto.

The electron transport layer (ETL) 111 may be formed on the emission layer (EL) 110 such that the electron transport layer (ETL) has a thickness of about 15 nm to about 50 nm, and may include tris(8-hydroxyquinolinato)aluminum (Alq3) and/or a material including a nitrogen-containing aromatic ring (for example, a material including a pyridine ring such as 1,3,5-tri[(3-pyridyl)-phen-3-yl]benzene, a material including a triazine ring such as 2,4,6-tris(3'-(pyridine-3-yl)biphenyl-3-yl)1,3,5-triazine, and a material including an imidazole derivative such as 2-(4-N-phenyl-benzoimidazolyl-1-ylphenyl)-9,10-dinaphthylanthracene).

The electron injection layer (EIL) 114 may be formed on the electron transport layer (ETL) 111 such that the electron injection layer (EIL) has a thickness of about 0.3 nm to about 9 nm, and may include, for example, lithium fluoride (LiF) and lithium-8-quinolinato (Liq), etc.

The cathode 116 may be on the electron injection layer (EIL) 114, and may include a metal (such as aluminum (Al), silver (Ag), lithium (Li), magnesium (Mg), calcium (Ca), and/or a mixture thereof), and/or a transparent material such as indium tin oxide (ITO) and/or indium zinc oxide ($In_2O_3$—ZnO).

Each electrode and each layer constituting the organic electroluminescent device according to an embodiment of the present disclosure as described above may be formed using an appropriate or suitable film-forming method such as vacuum deposition, sputtering, and other various coating methods (e.g., spin coating, casting, a Langmuir-Blodgett (LB) method, ink-jet printing, laser-printing, and/or laser-induced thermal imaging) depending on the materials to be used.

In the organic electroluminescent device 100 according to an embodiment of the present disclosure, when the material for an organic electroluminescent device according to an embodiment of the present disclosure is used to form a hole transport layer, the organic electroluminescent device may achieve long lifespan and high efficiency.

In the organic electroluminescent device 100 according to an embodiment of the present disclosure, the material for an organic electroluminescent device according to an embodiment of the present disclosure may be additionally used as a material for the hole injection layer. When the material for an organic electroluminescent device according to an embodiment of the present disclosure is included in at least one layer selected from a plurality of organic layers constituting the organic electroluminescent device, long lifespan and high efficiency of the organic electroluminescent device may be achieved.

The material for an organic electroluminescent device according to an embodiment of the present disclosure may be applied to an organic electroluminescent device in an active matrix using thin-film transistors (TFT).

Manufacturing Method

The material for an organic electroluminescent device according to an embodiment of the present disclosure may be synthesized as follows.

1. Synthetic Method of Compound 1

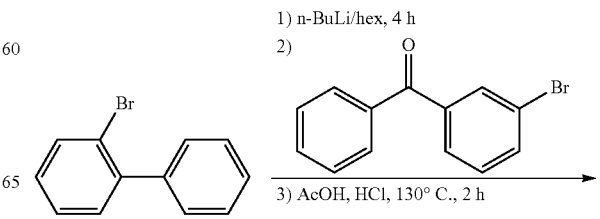

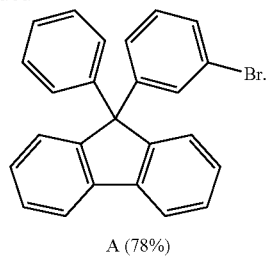

A (78%)

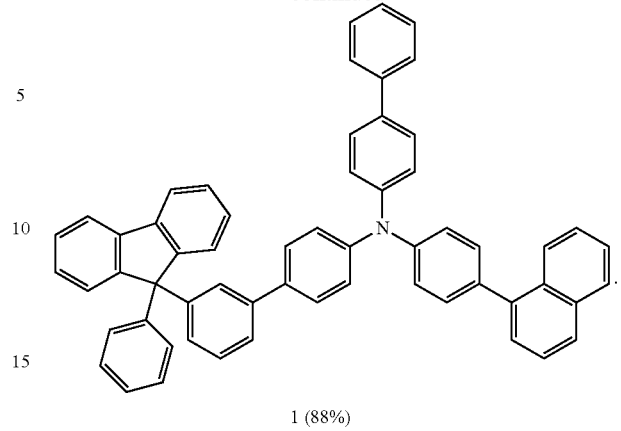

1 (88%)

Synthesis of Compound A

A solution of 10.0 g of 2-bromobiphenyl (42.9 mmol) in 70 mL of anhydrous THF was added to a 500 mL 3-neck flask and cooled to −78° C. 27 mL of a 1.58 M hexane solution of n-BuLi (42.9 mmol) was then added dropwise while stirring, and the reaction was stirred for about 2.5 hours. A solution of 9.30 g (35.6 mmol) of 3-bromobenzophenone in 85 mL of an anhydrous THF was added dropwise, and the resulting mixture was stirred for about 2 hours at −78° C. followed by stirring for about 3 hours at room temperature. 1 N hydrochloric acid (HCl) was then added to the mixture, and the mixture was stirred for about 1 hour. The mixture was washed with water, and the resultant organic phase was concentrated to afford a material having candy-like consistency. The candy-like material, 50 mL of acetic acid, and 2.4 mL of hydrochloric acid were added to a 500 mL recovery flask, and the mixture was stirred and reacted at 130° C. under a nitrogen atmosphere for about 2 hours. After the reaction, the reaction mixture was added dropwise to 350 mL of ice-cold water, precipitating white crystals, and the crystals were isolated by filtration. The crystals was washed with methanol and allowed to dry. About 13.3 g of Compound A was obtained as white powder (yield: about 78%). The molecular weight of Compound A measured through fast atom bombardment-mass spectrometry (FAB-MS) was about 397.

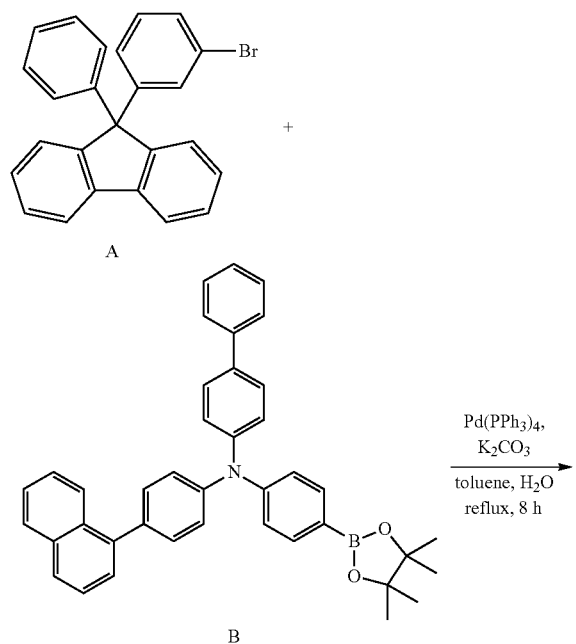

Synthesis of Compound 1

Under an Ar atmosphere, 1.70 g of compound A, 1.42 g of compound B, 0.263 g of Pd(PPh$_3$)$_4$, and 0.863 g of potassium carbonate were sequentially added to a 200 mL 3-neck flask, and the mixture was stirred in a mixed solvent of 50 mL toluene and 20 mL water at 90° C. for about 8 hours. The reaction was air cooled to room temperature, water was added to separate an organic phase, and the product was isolated by solvent distillation. The resultant crude product was purified using silica gel column chromatography (using a mixed solvent of dichloromethane and hexane), followed by recrystallization from a mixed solvent of toluene/hexane to yield about 2.18 g of Compound 1 (yield: about 88%) as a white solid.

The molecular weight of Compound 1 measured through FAB-MS was about 764. The $^1$H-NMR (CDCl$_3$) chemical shift value (δ) of Compound 1 was as follows: 8.55 (d, 2H, J=7.60 Hz), 8.42 (d, 1H, J=7.80 Hz), 8.08-8.06 (m, 2H), 7.89-7.86 (m, 2H), 7.79 (s, 1H), 7.63-7.51 (m, 15H), 7.41-7.25 (m, 10H), 7.11-7.07 (m, 3H), 6.73-6.61 (m, 6H).

2. Synthetic Method of Compound 17

Compound 17 was synthesized using substantially the same method as for Compound 1 except that 3'-bromoacetophenone was used instead of 3-bromobenzophenone in the synthesis of intermediate Compound A. The molecular weight of compound 17 measured through FAB-MS was about 702. The $^1$H-NMR (CDCl$_3$) chemical shift value (δ) of compound 17 was as follows: 8.57 (d, 2H, J=7.60 Hz), 8.44 (d, 1H, J=7.80 Hz), 8.10-8.08 (m, 2H), 7.89-7.82 (m, 3H), 7.61-7.25 (m, 23H), 7.01-6.76 (m, 6H), 2.33 (s, 3H).

3. Synthesis of Compound 9

Intermediate A was synthesized using substantially the same method used for Compound 1. Under an Ar atmosphere, 3.30 g of Compound A, 2.82 g of Compound C, 0.530 g of Pd(PPh$_3$)$_4$, and 1.72 g of potassium carbonate were sequentially added to a 200 mL 3-neck flask, and the mixture was stirred in a mixed solvent of 70 mL toluene and 25 mL water at 90° C. for about 8 hours. The reaction was air cooled to room temperature, water was added to separate an organic phase, and the product was isolated by solvent distillation. The resulting crude product was purified using silica gel column chromatography (using a mixed solvent of dichloromethane and hexane), followed by recrystallization from a mixed solvent of toluene/hexane to yield about 4.44 g of Compound 9 (yield: about 70%) as a white solid.

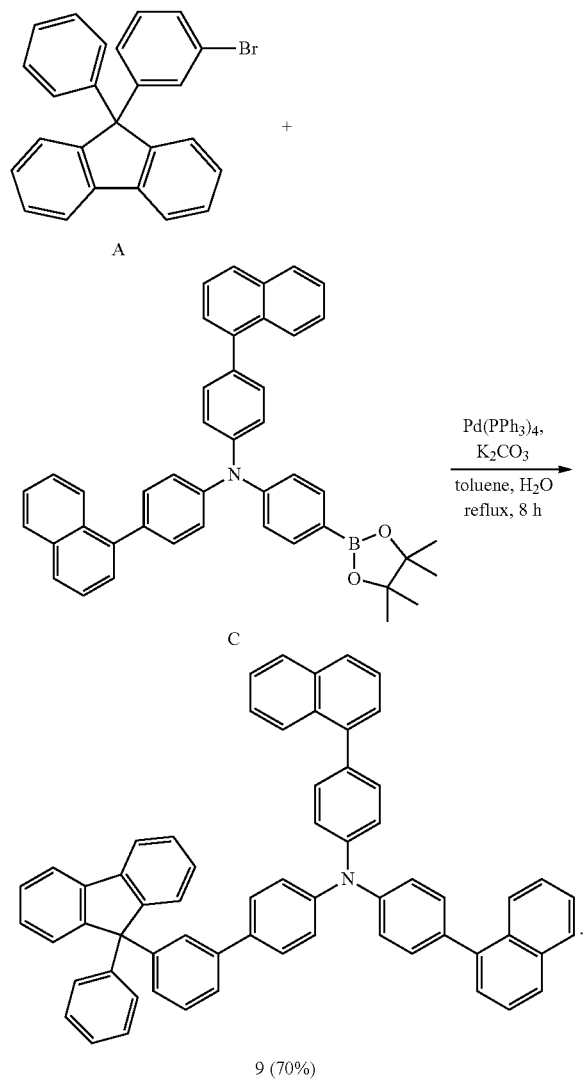

The molecular weight of Compound 9 measured through FAB-MS was about 814. The $^1$H-NMR (CDCl$_3$) chemical shift value (δ) of Compound 9 was as follows: 8.55 (d, 2H, J=7.60 Hz), 8.44 (d, 2H, J=7.70 Hz), 8.13-8.00 (m, 4H), 7.55-7.50 (m, 2H), 7.89-7.82 (m, 2H), 7.79 (s, 1H), 7.61-7.52 (m, 14H), 7.41-7.25 (m, 8H), 7.11-7.07 (m, 3H), 6.77-6.52 (m, 6H).

4. Synthesis of Compound 33

Intermediate A was synthesized using substantially the same method used for Compound 1. Under an Ar atmosphere, 5.70 g of Compound A, 6.00 g of Compound D, 0.563 g of Pd(dba)$_2$, 0.23 g of (t-Bu)$_3$P, and 4.13 g of sodium t-butoxide were added to a 200 mL 3-neck flask, and the mixture was stirred, heated, and refluxed in 140 mL of toluene for about 8 hours. The reaction was air cooled to room temperature, water was added to separate an organic phase, and the product was isolated by solvent distillation. The resulting crude product was purified using silica gel column chromatography (using a mixed solvent of toluene and hexane), followed by recrystallization from a mixed solvent of toluene/hexane to yield about 10.7 g of Compound 33 (yield: about 90%) as a white solid.

The molecular weight of Compound 33 measured through FAB-MS was about 738. The $^1$H-NMR (CDCl$_3$) chemical shift value (δ) of Compound 33 was as follows: 8.56 (d, 2H, J=7.60 Hz), 8.40 (d, 1H, J=7.80 Hz), 8.05-8.02 (m, 2H), 7.87-7.84 (m, 4H), 7.80 (s, 1H), 7.70-7.50 (m, 11H), 7.40-7.27 (m, 10H), 7.16-7.11 (m, 3H), 7.08-7.03 (m, 6H).

5. Synthesis of Compound 34

Intermediate A was synthesized using substantially the same method used for Compound 1. Under an Ar atmosphere, 6.42 g of Compound A, 6.00 g of Compound E, 0.563 g of Pd(dba)$_2$, 0.87 g of (t-Bu)$_3$P, and 4.66 g of sodium t-butoxide were added to a 200 mL 3-neck flask, and the mixture was stirred, heated, and refluxed in 150 mL of toluene for about 8 hours. The reaction was air cooled to room temperature, water was added to separate an organic phase, and the product was isolated by solvent distillation. The resulting crude product was purified using silica gel column chromatography (using a mixed solvent of dichloromethane and hexane), followed by recrystallization from a mixed solvent of toluene/hexane to yield about 9.44 g of Compound 34 (yield: about 85%) as a white solid.

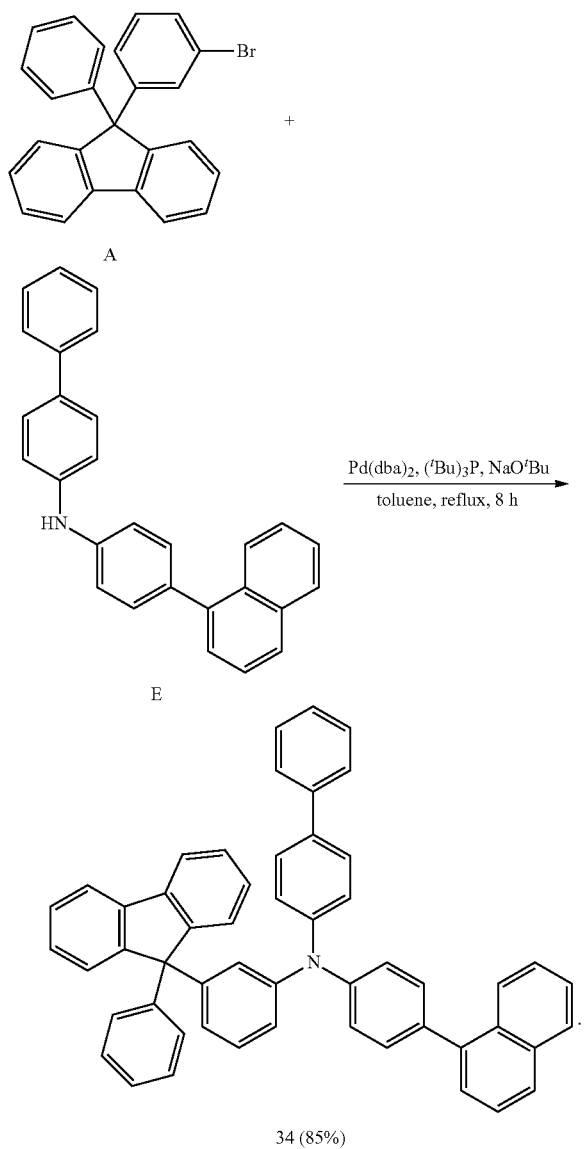

34 (85%)

The molecular weight of Compound 34 measured through FAB-MS was about 688. The $^1$H-NMR (CDCl$_3$) chemical shift value (δ) of Compound 34 was as follows: 8.53 (d, 2H, J=7.60 Hz), 8.40 (d, 1H, J=7.80 Hz), 8.05-8.02 (m, 2H), 7.85-7.83 (m, 2H), 7.80 (s, 1H), 7.73-7.51 (m, 11H), 7.40-7.25 (m, 10H), 7.16-7.09 (m, 3H), 7.07-7.02 (m, 6H).

6. Synthesis of Compound 58

Intermediate A was synthesized using substantially the same method used for Compound 1. Under an Ar atmosphere, 3.00 g of Compound A, 3.22 g of Compound F, 0.510 g of Pd(PPh$_3$)$_4$, and 1.62 g of potassium carbonate were sequentially added to a 200 mL 3-neck flask, and the mixture was stirred in a mixed solvent of 70 mL toluene and 25 mL water at 90° C. for about 8 hours. The reaction was air cooled, water was added to separate an organic phase, and the product was isolated by solvent distillation. The resultant crude product was purified by silica gel column chromatography (using a mixed solvent of dichloromethane and hexane), followed by recrystallization from a mixed solvent of toluene/hexane to yield about 3.04 g of Compound 58 (yield: about 70%) as a white solid.

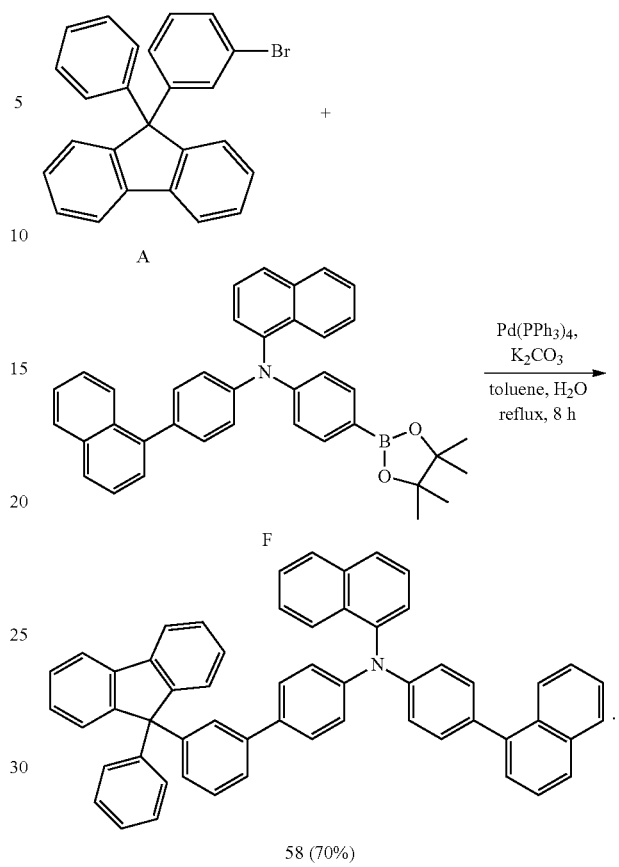

58 (70%)

The molecular weight of Compound 58 measured through FAB-MS was about 738. The $^1$H-NMR (CDCl$_3$) chemical shift value (δ) of Compound 58 was as follows: 8.58 (d, 2H, J=7.60 Hz), 8.30 (d, 1H, J=7.80 Hz), 8.05-8.02 (m, 2H), 7.88-7.83 (m, 2H), 7.75 (s, 1H), 7.63-7.51 (m, 11H), 7.40-7.25 (m, 10H), 7.16-7.09 (m, 3H), 7.08-7.02 (m, 4H).

7. Synthesis of Compound 49

Compound 49 was synthesized using substantially the same method as for Compound 34, except that N-[4-(1-naphthalenyl)phenyl]-1-naphthalenamine was used instead of Compound E. The molecular weight of compound 49 measured through FAB-MS was about 662. The $^1$H-NMR (CDCl$_3$) chemical shift value (δ) of Compound 49 was as follows: 8.48 (d, 2H, J=7.50 Hz), 8.30 (d, 1H, J=7.80 Hz), 8.05-8.02 (m, 2H), 7.88-7.83 (m, 2H), 7.70 (s, 1H), 7.60-7.50 (m, 7H), 7.41-7.28 (m, 10H), 7.16-7.11 (m, 3H), 7.08-7.05 (m, 4H).

8. Synthesis of Compound 50

Compound 50 was synthesized using substantially the same method as for Compound 34, except that N-[1,1'-biphenyl]-4-yl-1-naphthalenamine was used instead of Compound E. The molecular weight of compound 50 measured through FAB-MS was about 612. The $^1$H-NMR (CDCl$_3$) chemical shift value (δ) of compound 50 was as follows: 8.45 (d, 2H, J=7.50 Hz), 8.30 (d, 1H, J=7.80 Hz), 7.80 (s, 1H), 7.60-7.50 (m, 7H), 7.41-7.28 (m, 10H), 7.26-7.11 (m, 3H), 7.08-7.05 (m, 4H).

The organic electroluminescent devices of Examples 1 to 8 were manufactured using the above-described manufacturing methods with Compounds 1, 17, 9, 33, 34, 49, 50, and 58, respectively, as hole transport materials.

1
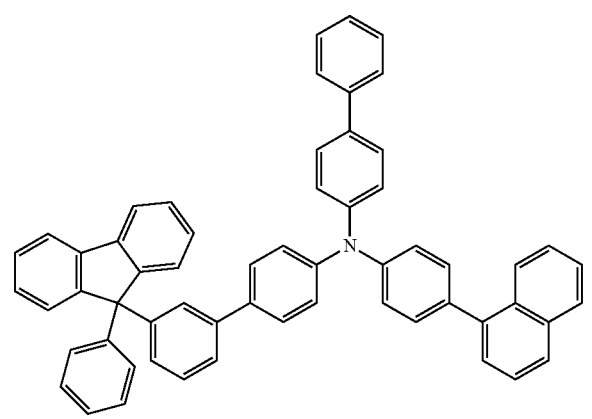
17
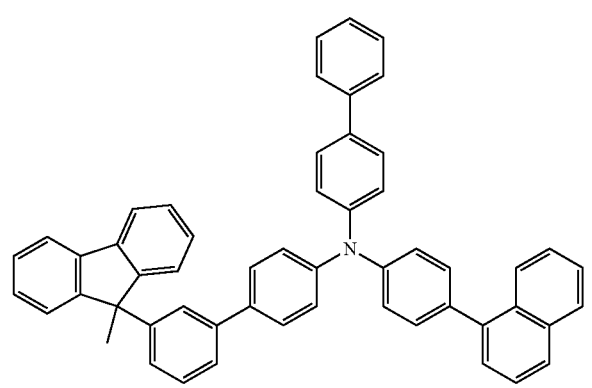
9
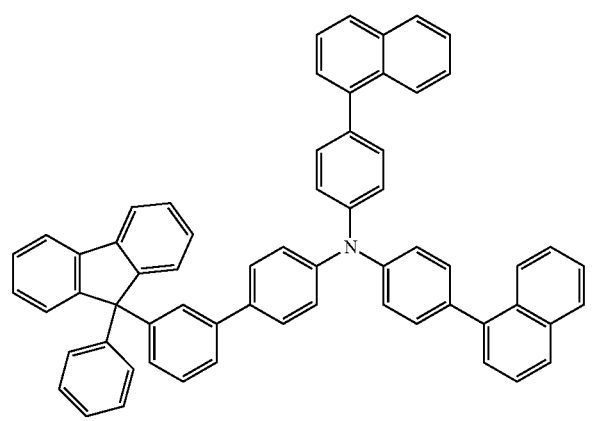
33
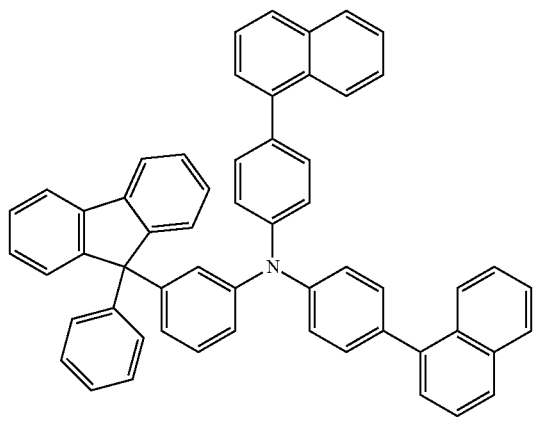
34
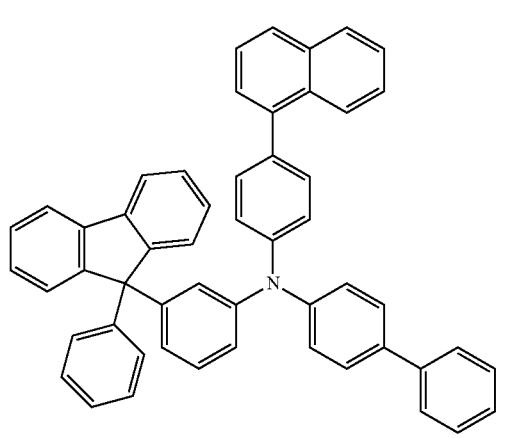
49
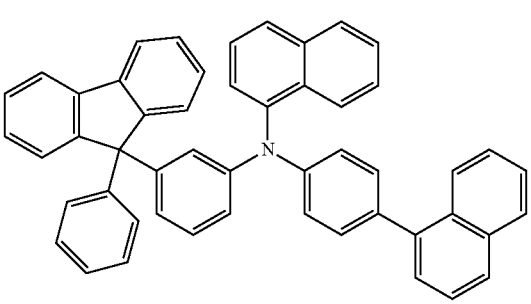
50
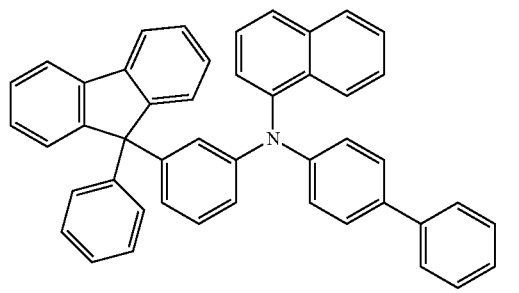

58
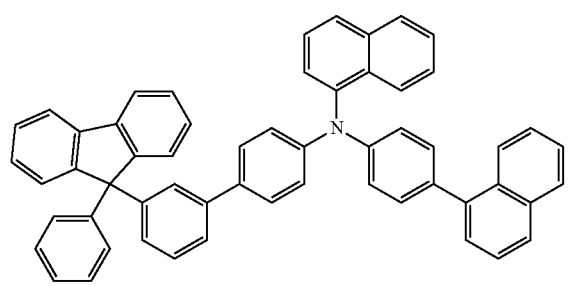
Furthermore, the organic electroluminescent devices of Comparative Examples 1 to 7 were manufactured using Comparative Example Compounds A-1 to A-7, respectively, as hole transport materials.
Comparative Example Compounds
A-1
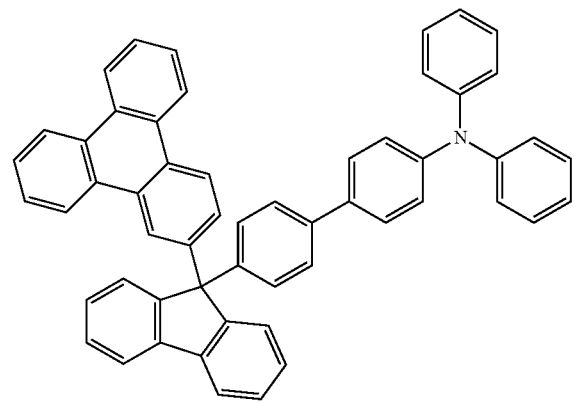
A-2
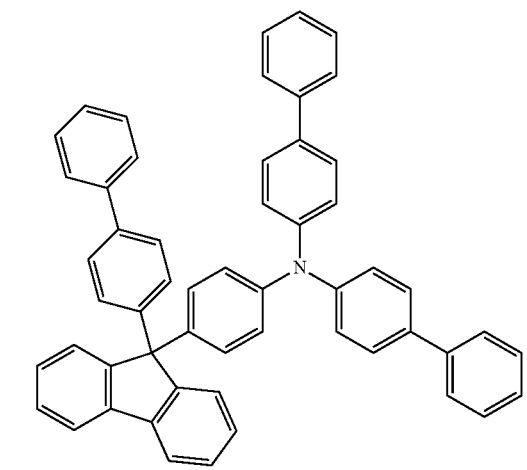
A-3
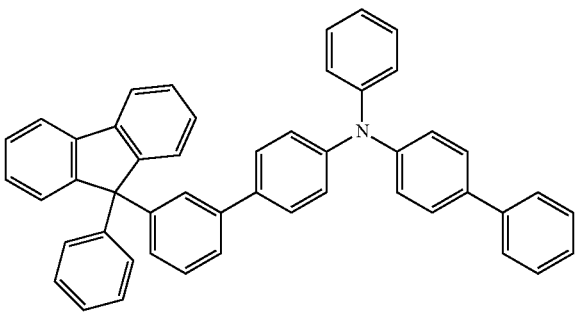
A-4
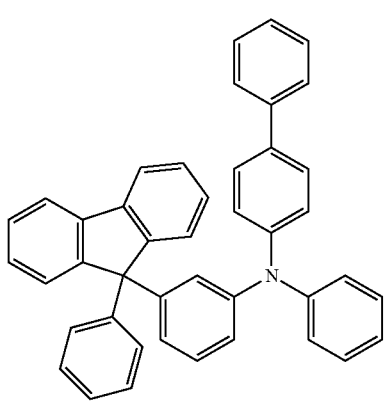
A-5
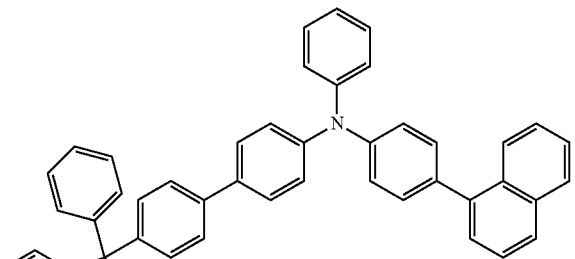
A-6
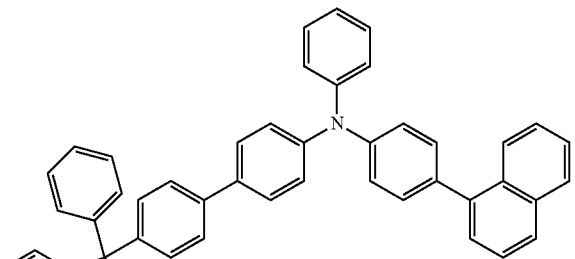

-continued

A-7

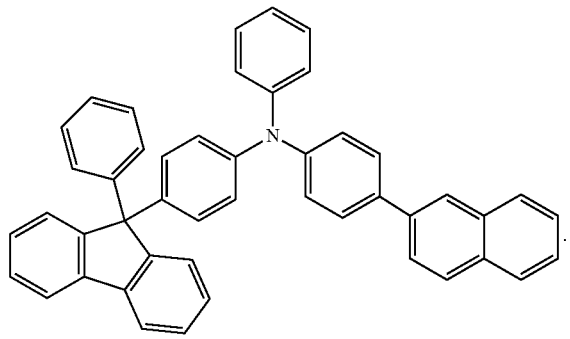

Figure 2:
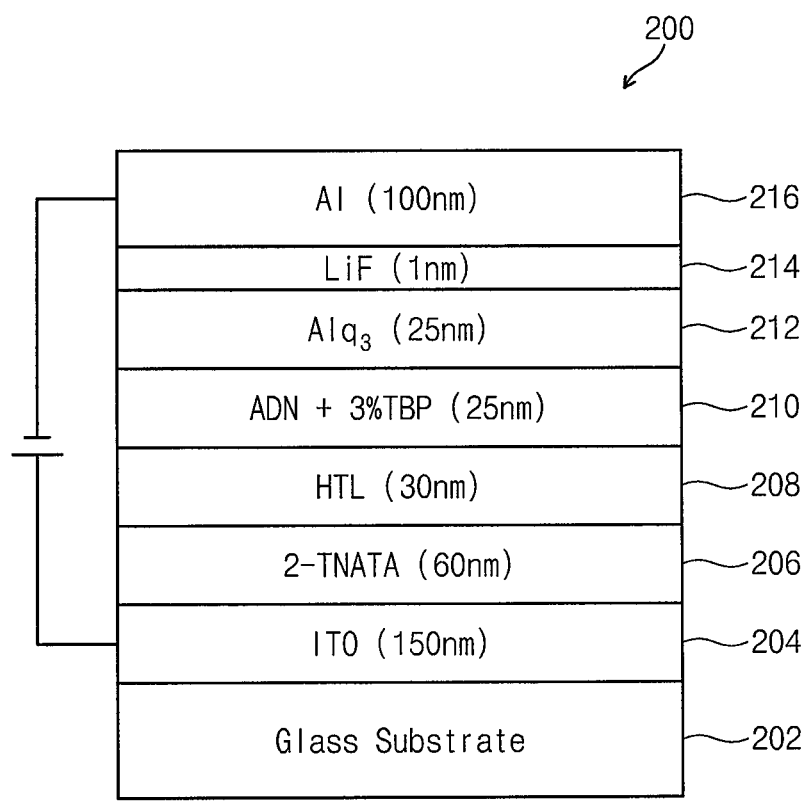
FIG. 2 is a schematic diagram showing an organic electroluminescent device according to an embodiment of the present disclosure.

FIG. 2 is a schematic drawing illustrating the structure of an organic electroluminescent device 200 according to an example embodiment of the present disclosure. In the present example organic electroluminescent devices, a transparent glass substrate was used as a substrate 202. An anode 204 having a film thickness of about 150 nm was formed using ITO. A hole injection layer 206 having a film thickness of about 60 nm was formed using 2-TNATA. A hole transport layer 208 having a film thickness of about 30 nm was formed using the hole transport material shown in Table 1. An emission layer 210 having a film thickness of about 25 nm was formed by coating ADN with 3% TBP. An electron transport layer 212 having a film thickness of about 25 nm was formed using Alq3. An electron injection layer 214 having a film thickness of about 1 nm was formed using LiF. A cathode 216 having a film thickness of about 100 nm was formed using Al.

The emission efficiencies and half-lives of the manufactured example organic electroluminescent devices were evaluated. The voltage and emission efficiencies were measured at a current density of about 10 mA/cm². The half-life indicates the time elapsed until the brightness decreased to about half the initial brightness of about 1,000 cd/m². The evaluation results are shown in Table 1 below:

TABLE 1

| Example device | Hole transport material | Emission efficiency (cd/A) | Half-life LT50 (h) |
| --- | --- | --- | --- |
| Example 1 | Compound 1 | 6.7 | 2,100 |
| Example 2 | Compound 17 | 6.7 | 1,950 |
| Example 3 | Compound 9 | 6.5 | 2,000 |
| Example 4 | Compound 33 | 6.6 | 2,000 |
| Example 5 | Compound 34 | 6.6 | 2,000 |
| Example 6 | Compound 49 | 6.7 | 1,950 |
| Example 7 | Compound 50 | 6.6 | 1,950 |
| Example 8 | Compound 58 | 6.7 | 2,000 |
| Comparative Example 1 | Comparative Example Compound A-1 | 5.2 | 1,500 |
| Comparative Example 2 | Comparative Example Compound A-2 | 5.0 | 1,550 |
| Comparative Example 3 | Comparative Example Compound A-3 | 5.5 | 1,300 |
| Comparative Example 4 | Comparative Example Compound A-4 | 5.5 | 1,400 |
| Comparative Example 5 | Comparative Example Compound A-5 | 5.6 | 1,550 |
| Comparative Example 6 | Comparative Example Compound A-6 | 5.5 | 1,500 |
| Comparative Example 7 | Comparative Example Compound A-7 | 5.5 | 1,500 |

Referring to the results in Table 1, the half-lives (e.g., lifespans) and efficiencies of Examples 1 to 8 are improved with respect to Comparative Examples 1 to 7. In these examples, the material for an organic electroluminescent device according to an embodiment of the present disclosure contains a fluorenyl group and a naphthyl group linked (e.g., coupled) to an amine, and may thereby achieve long device lifespans because the favorable hole transporting properties of the amine are maintained and combined with the high charge resistance of the fluorenyl and naphthyl groups. In addition, pi conjugation around the amine may improve stability to radicals, which may contribute to longer lifespans. Further, in the material for an organic electroluminescent device according to an embodiment of the present disclosure, when the fluorenyl group is linked (e.g., coupled) to the amine moiety via an m-phenylene group, the molecular symmetry of the material may be destroyed and the amorphous nature of the compound may be enhanced, thereby improving the emission efficiency of the material. Also, since the quaternary carbon (e.g., of the fluorene group) and the nitrogen atom (e.g., of the amine) are located at meta positions, radical-induced degradation of the compound may be inhibited or reduced, and long lifespan may be achieved. In Comparative Examples 1 and 2, the directly substituted fluorene group has a larger volume than a phenyl group (e.g., a fluorene group linked via a phenyl group), such that steric hindrance between the fluorene group and the amine unit is greater, resulting in compound instability and a decline in lifespan and efficiency. Comparative Examples 3 and 4 have short lifespans, which may be due to the lesser degree of pi conjugation around the amine. Although Comparative Examples 5 to 7 have naphthyl groups, the presence of quaternary carbons para to the nitrogen atom of the amine may decrease the stability of the radical state, thereby leading to a shorter lifespan. It has been considered that the lifespan in Example 2 is shorter than other examples because Compound 17 has a methyl group and thereby exhibits insufficient heat resistance.

From the results in Table 1, it has been demonstrated that when the material for an organic electroluminescent device according to an embodiment of the present disclosure is used as a hole transport material, these devices exhibit higher efficiencies and longer lifespans compared to Comparative Example devices. The material for an organic electroluminescent device according to an embodiment of the present disclosure may achieve high efficiency and long lifespan when a fluorenyl group and naphthyl group having high charge resistance are introduced (e.g., coupled) to an amine.

The material for an organic electroluminescent device according to an embodiment of the present disclosure may have a broad energy gap, and the material may be applied to devices in the red and green light-emitting regions.

The present disclosure provides a material for an organic electroluminescent device having a high emission efficiency and long lifespan, and an organic electroluminescent device including the material. In the material for an organic electroluminescent device of the present disclosure, a fluorenyl group and naphthyl group having high charge resistance are introduced (e.g., coupled) to an amine moiety so that degradation of the material may be inhibited and long lifespan may be achieved. Further, when the amine is substituted with a fluorenyl group via an m-phenylene linker, the molecular symmetry of the material may be destroyed, and the amorphous nature of the compound may be enhanced, thereby improving the emission efficiency. This effect may be particularly significant in the blue light-emitting region.

As used herein, expressions such as "at least one of", "one of", "at least one selected from", and "one selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more example embodiments of the present disclosure have been described with reference to the drawings, it will be understood by those of ordinary skill in the art that various changes in form and details may be made therein without departing from the spirit and scope of the present disclosure as defined by the following claims and equivalents thereof.

What is claimed is:

1. A material for an organic electroluminescent device represented by Formula 1:

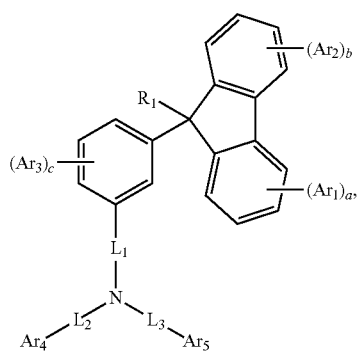

Formula 1 wherein,
R₁ is selected from a substituted or unsubstituted aryl group having 6 to 10 carbon atoms for forming a ring and an alkyl group having 1 to 20 carbon atoms;
Ar₁ to Ar₅ are each independently selected from a substituted or unsubstituted aryl group having 6 to 30 carbon atoms for forming a ring, a substituted or unsubstituted heteroaryl group having 5 to 30 carbon atoms for forming a ring, an alkyl group having 1 to 20 carbon atoms, a silyl group, a halogen atom, deuterium, and hydrogen;
at least one selected from Ar₄ and Ar₅ is a substituted or unsubstituted naphthyl group;
L₁ to L₃ are each independently selected from a single-bond and a substituted or unsubstituted arylene group having 6 to 12 carbon atoms for forming a ring;
L₁ is selected so that the quaternary carbon of the fluorenyl group and the nitrogen atom of the amine are at meta positions; and
a to c are each independently an integer selected from 0 to 4.

2. The material for an organic electroluminescent device of claim 1, wherein R₁ is selected from a substituted or unsubstituted phenyl group and a substituted or unsubstituted naphthyl group.

3. The material for an organic electroluminescent device of claim 1, wherein at least one selected from L₁ to L₃ is a phenylene group.

4. The material for an organic electroluminescent device of claim 1, wherein the material for an organic electroluminescent device represented by Formula 1 above is further represented by at least one selected from Compounds 1 to 60:

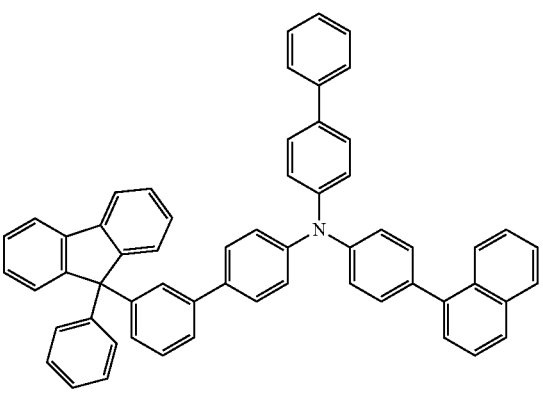

1

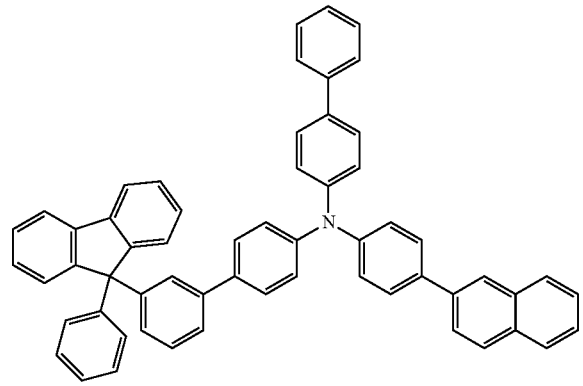

2

3
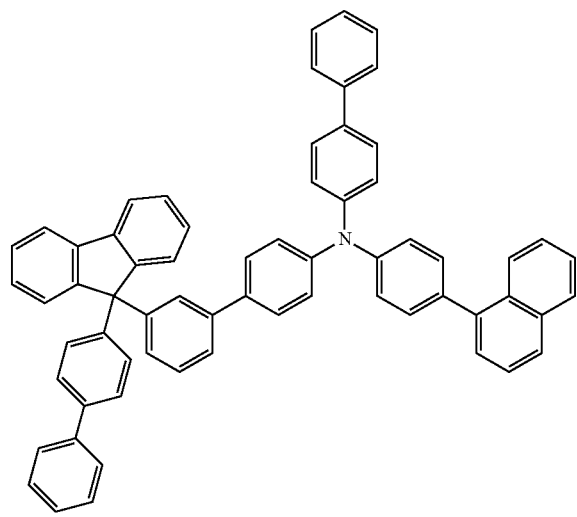
4
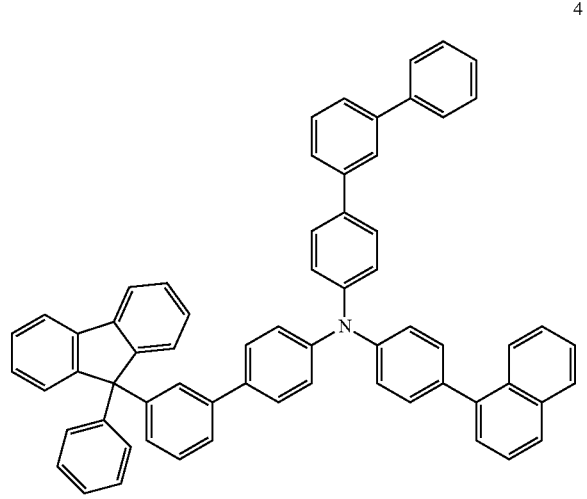
5
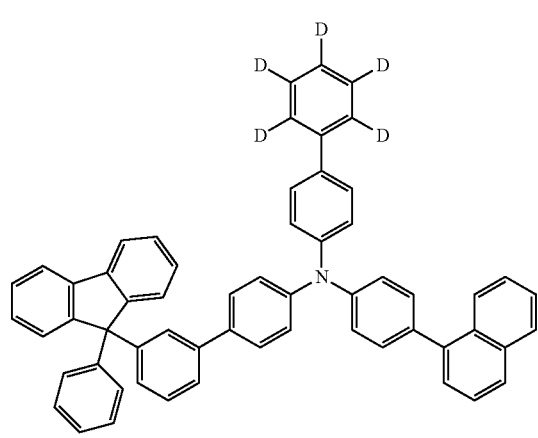
6
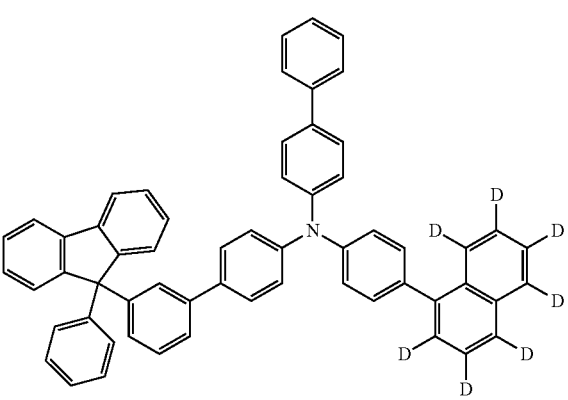
7
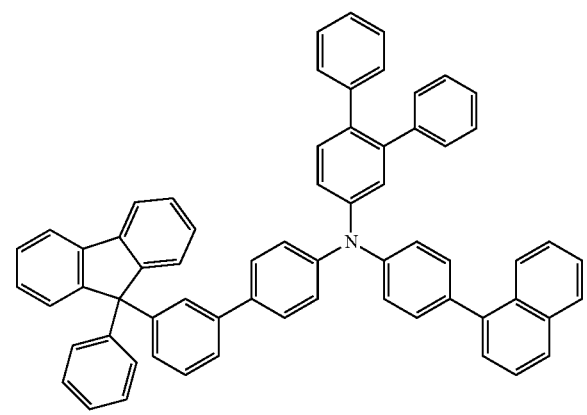
8

9
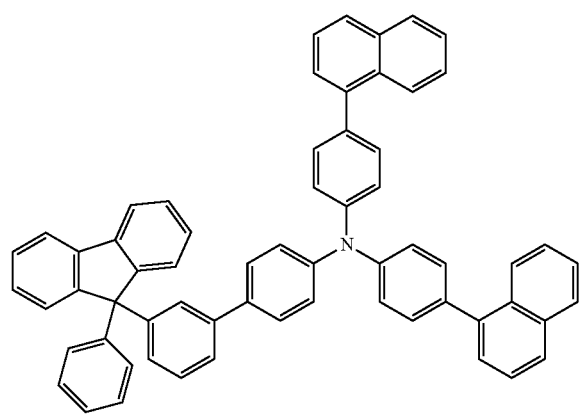
10
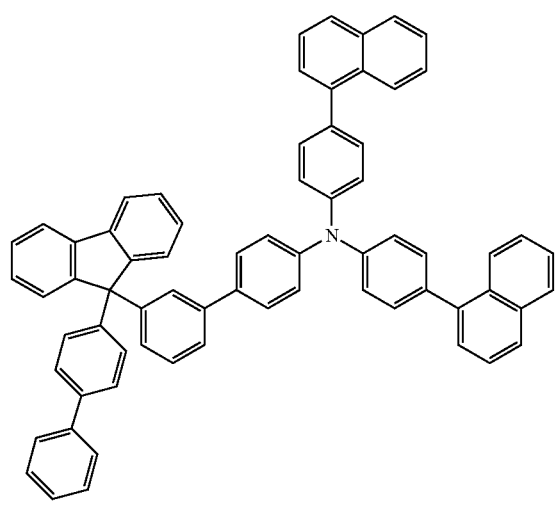
11
12
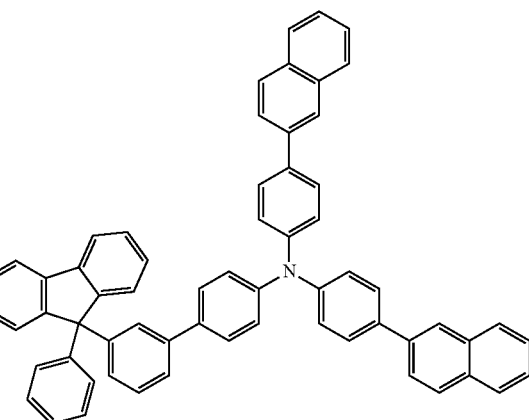
13
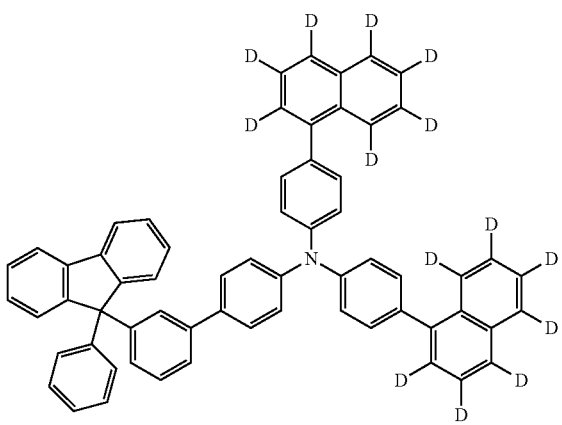
14
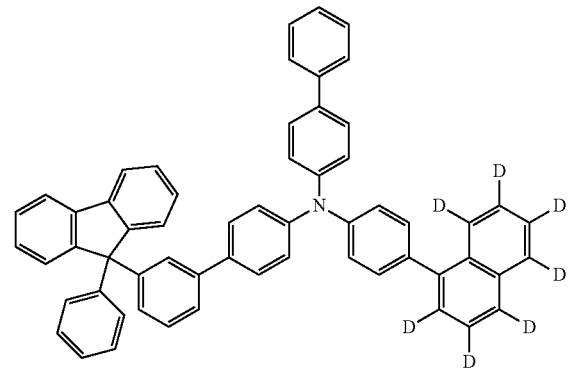

15
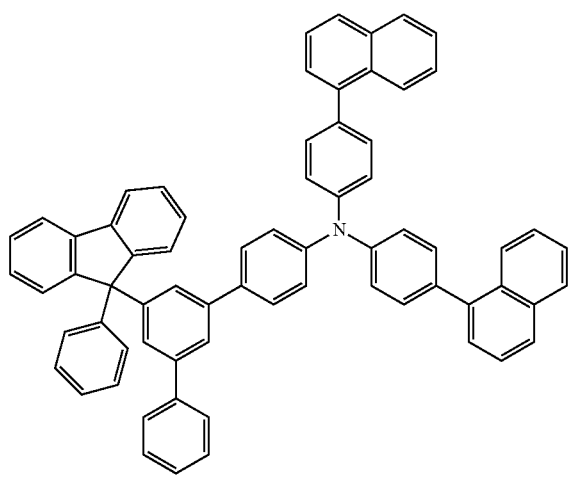
16
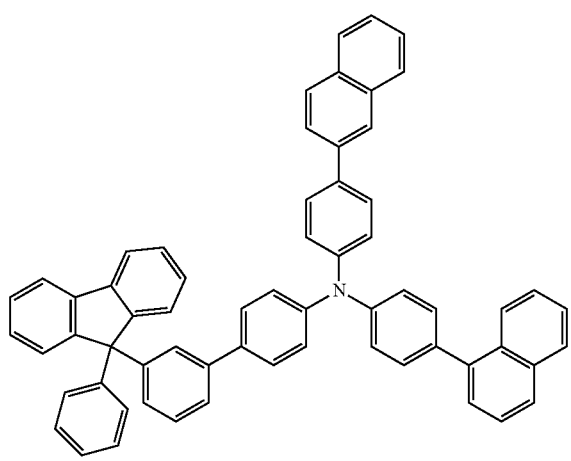
17
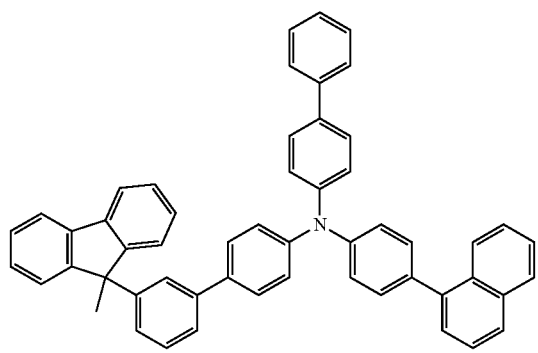
18
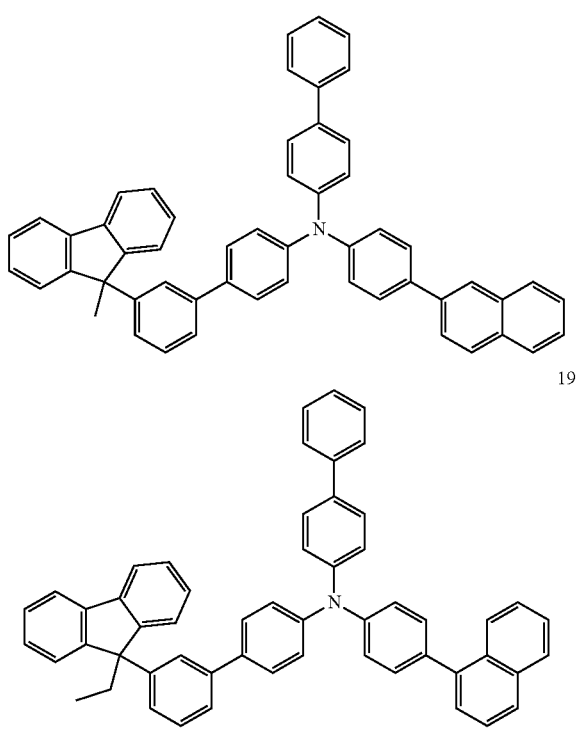
19
20
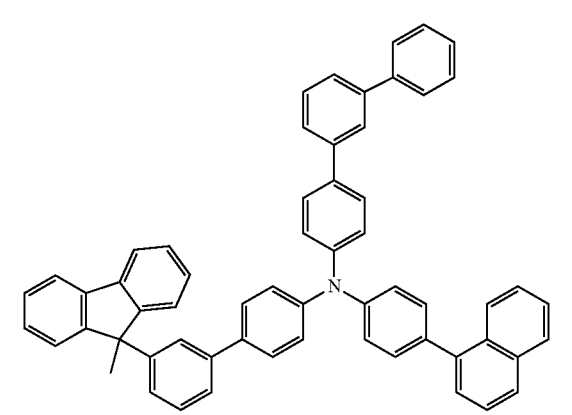
21
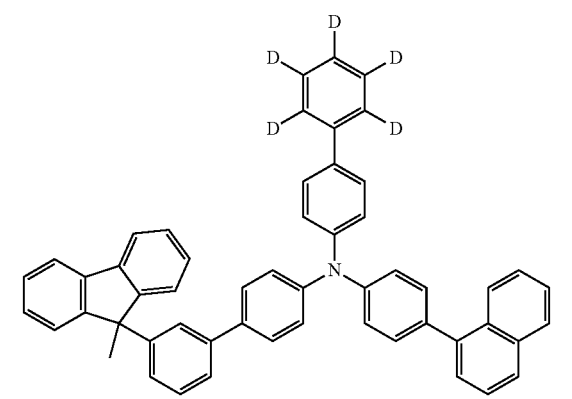

22
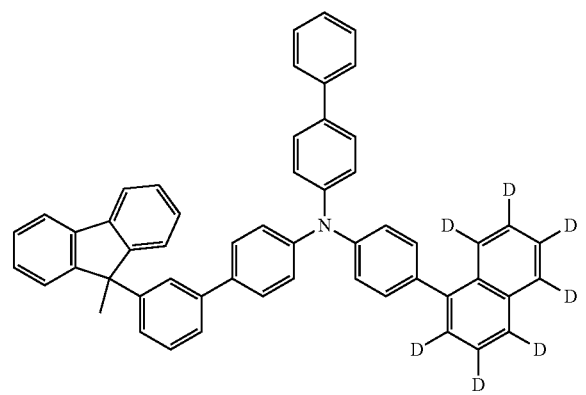
23
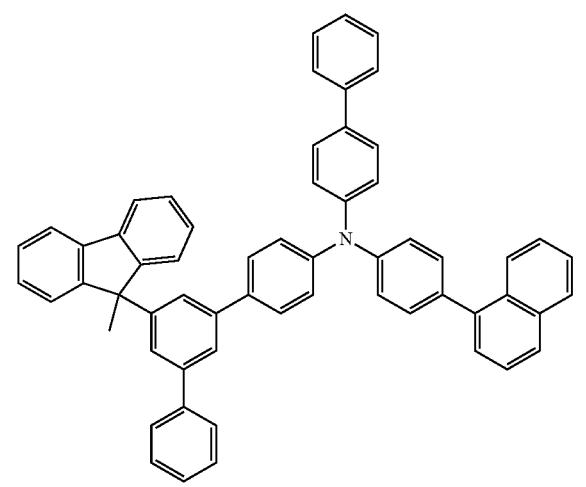
24
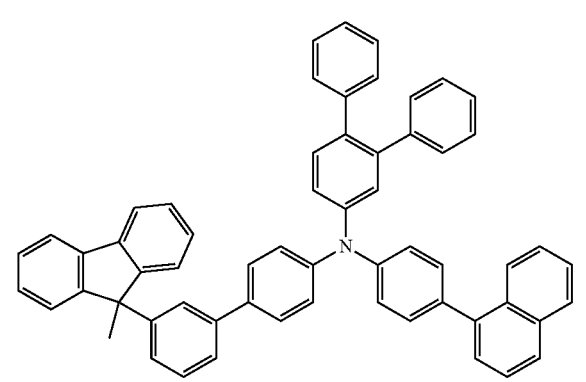
25
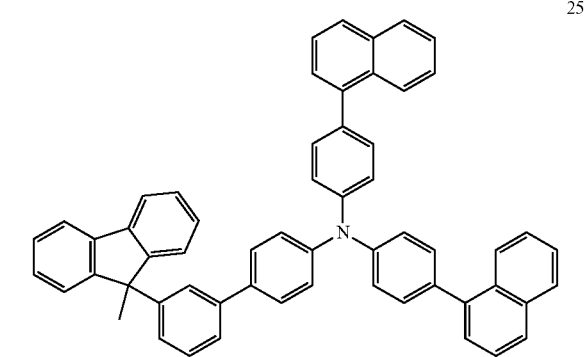
26
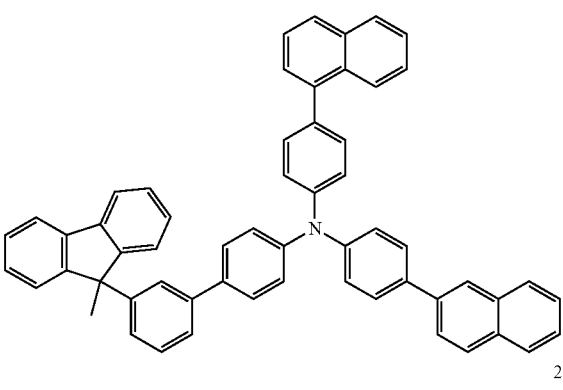
27
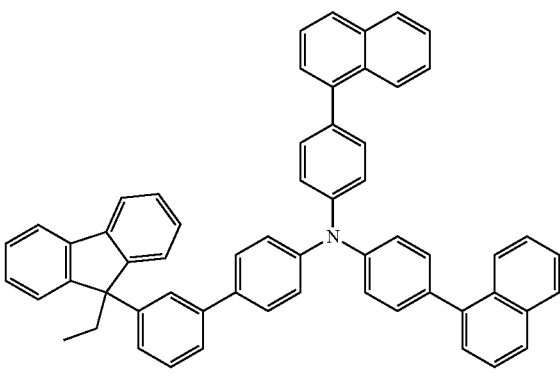
28
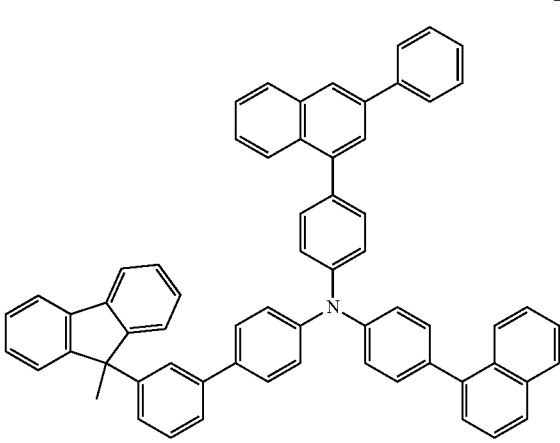
29
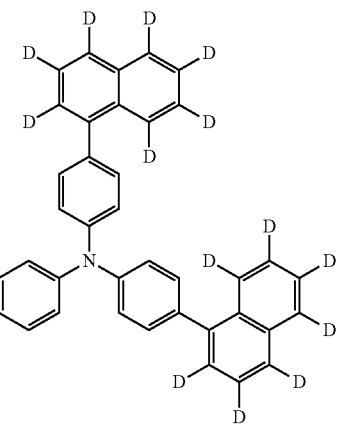

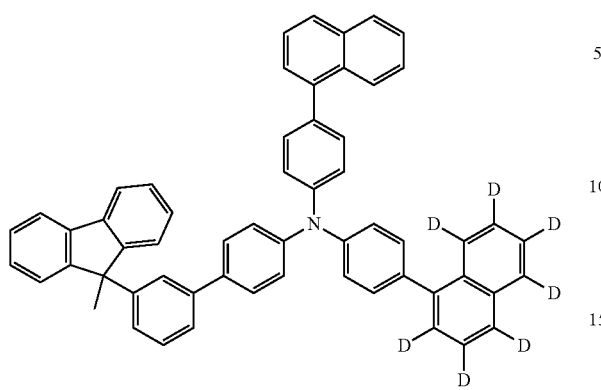
30
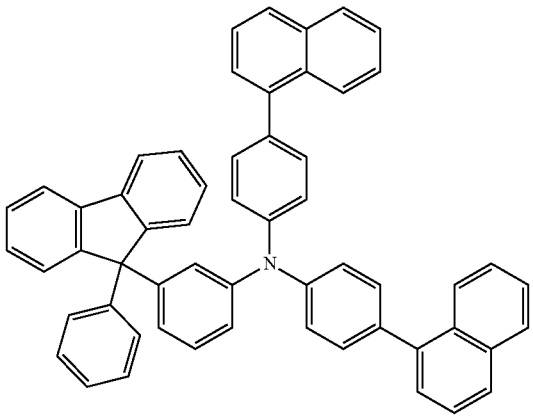
33
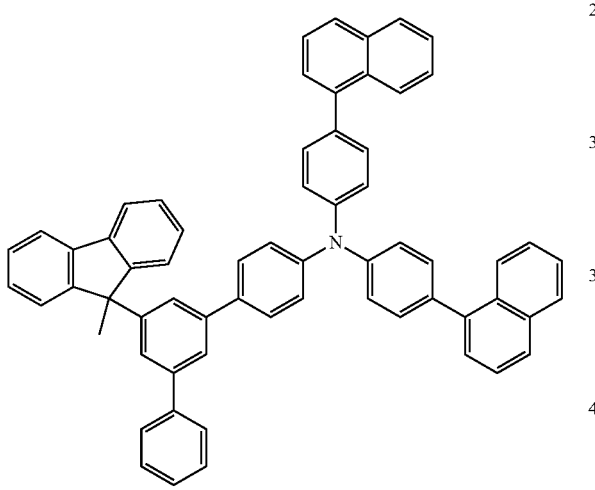
31
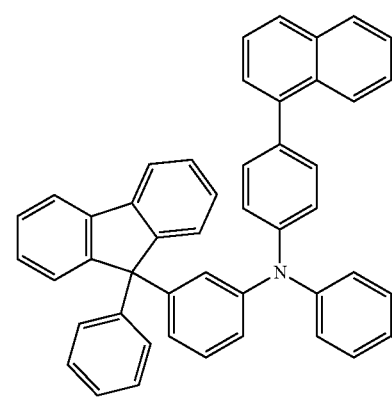
34
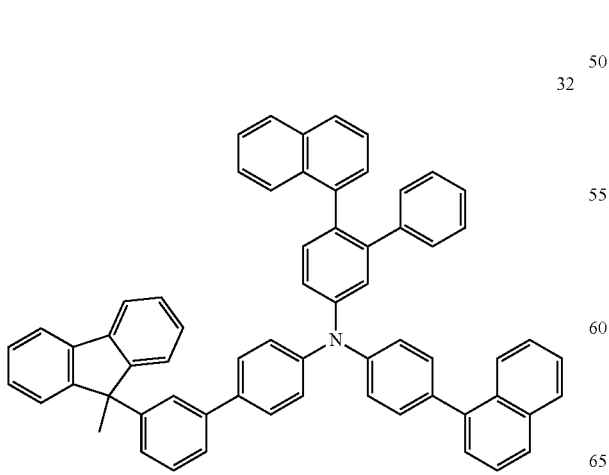
32
36

37
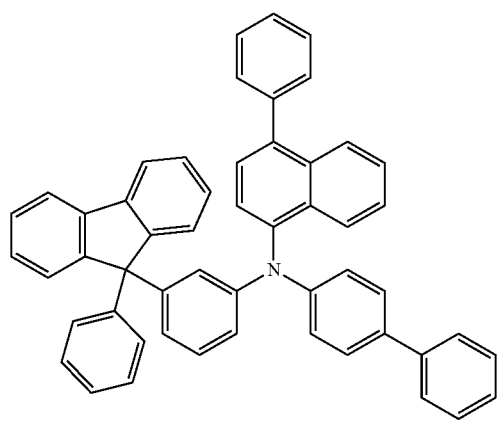
38
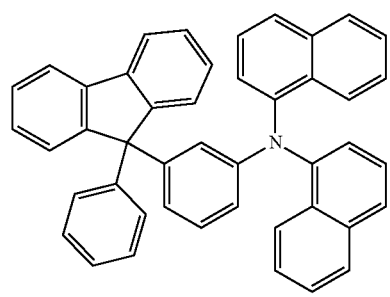
39
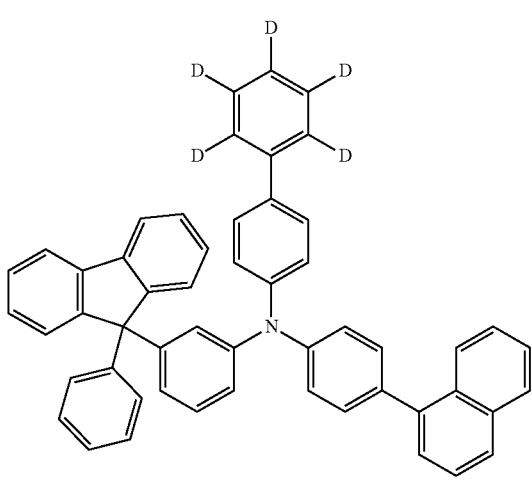
40
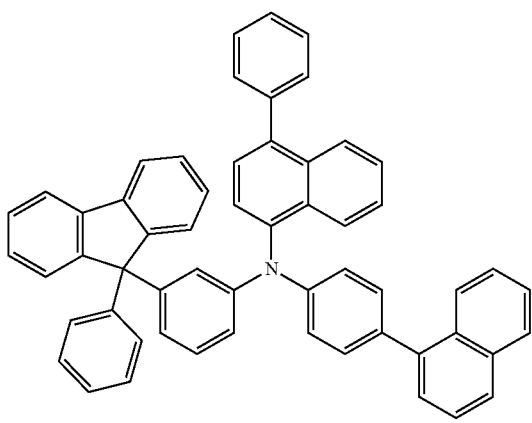
41
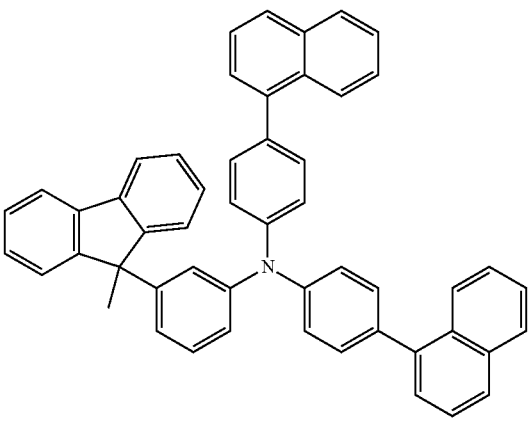
42
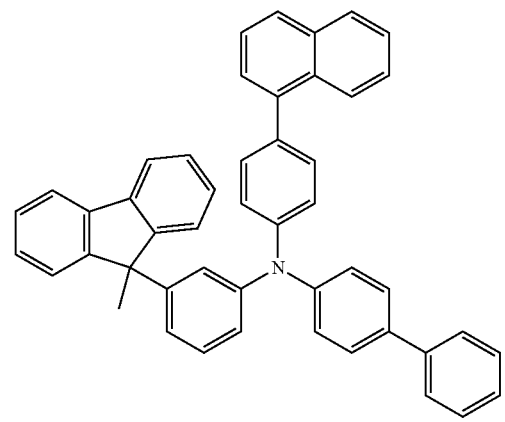
44
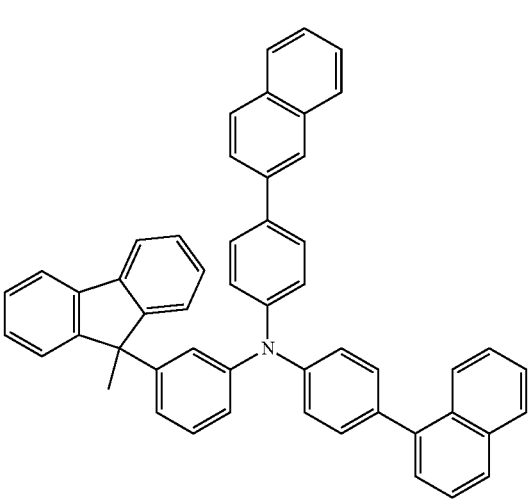

45
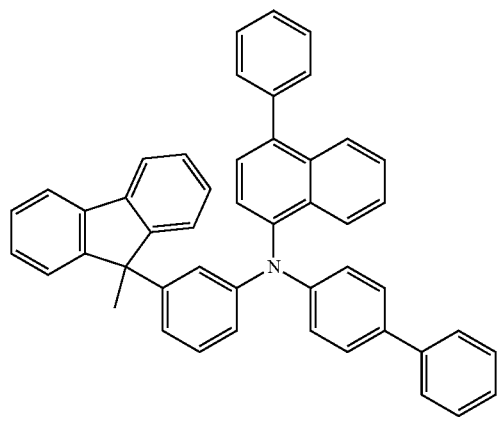
46
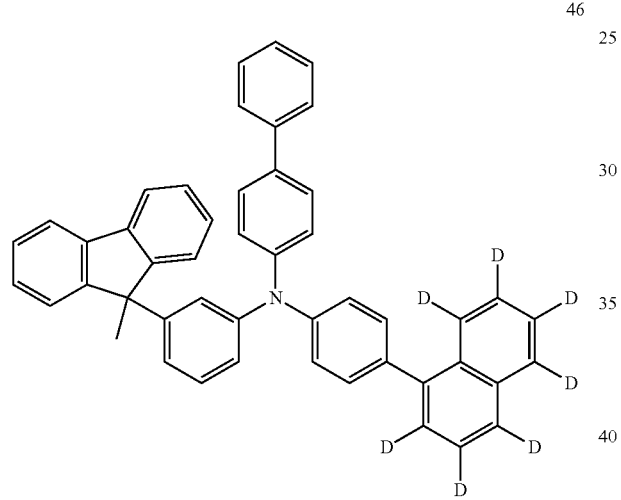
47
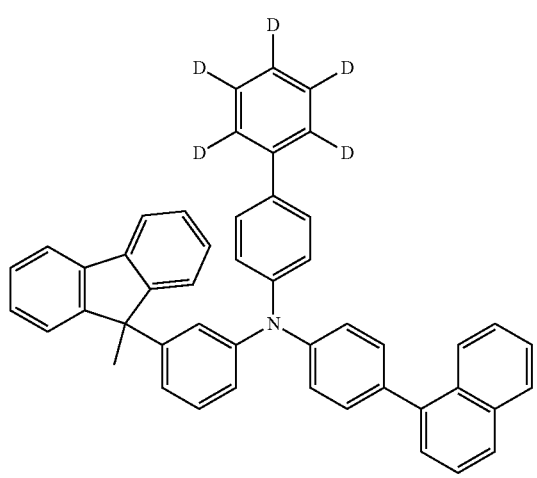
48
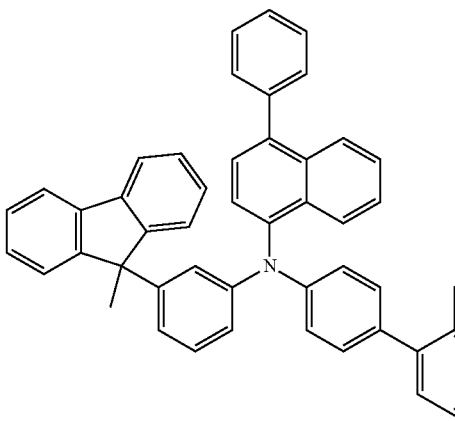
49
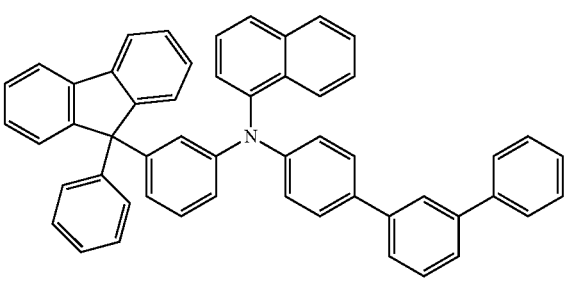
50
51

52
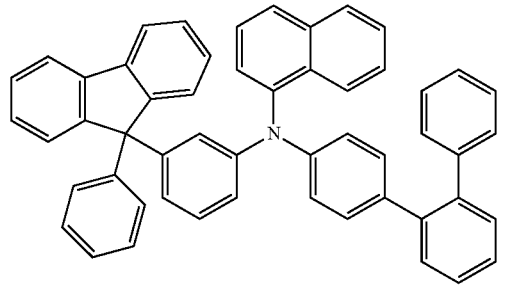
53
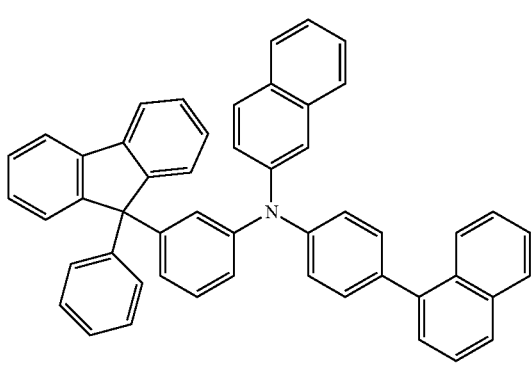
54
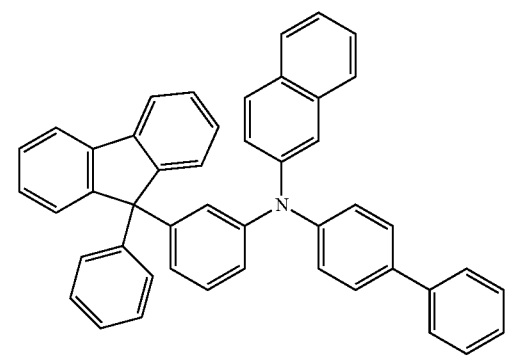
55
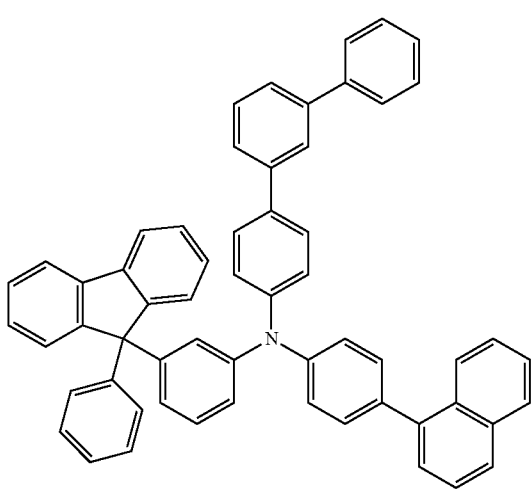
56
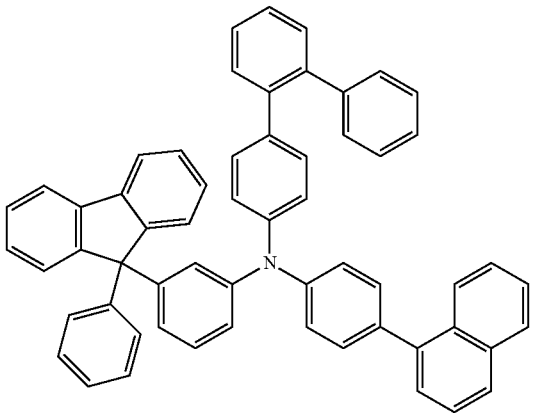
57
58
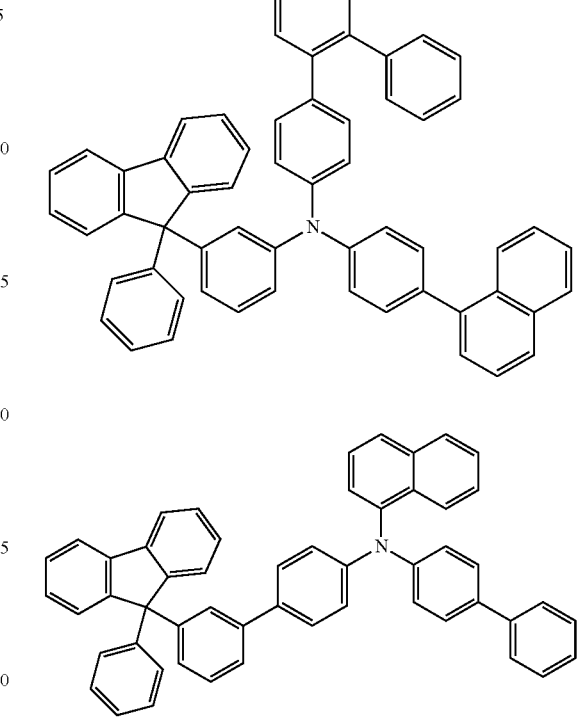
59
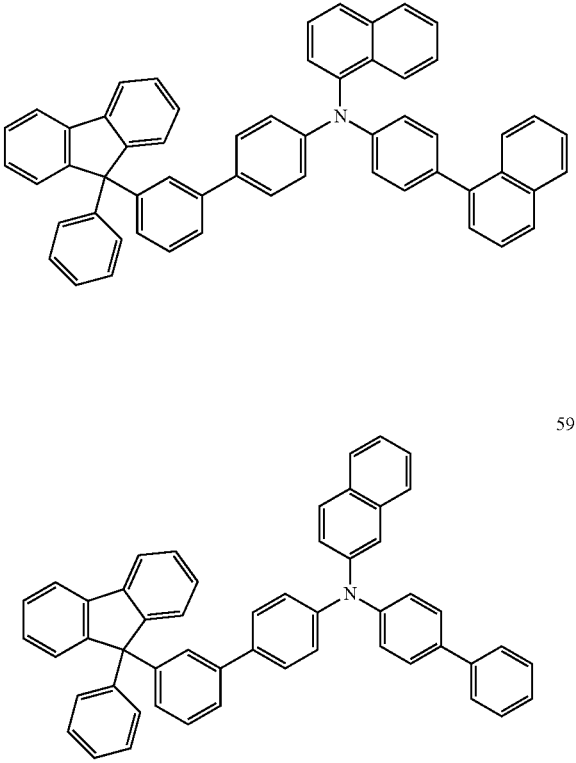

-continued

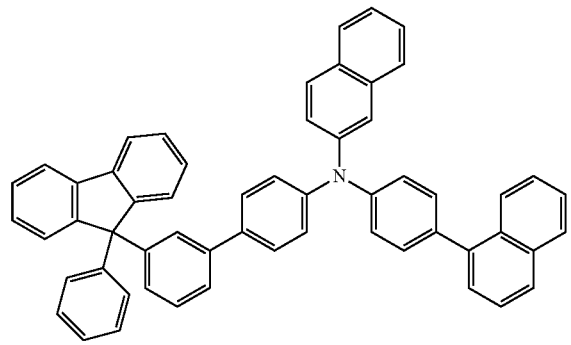

5. An organic electroluminescent device, comprising:
a first electrode;
a second electrode facing the first electrode; and
one or more organic layers between the first electrode and the second electrode, wherein at least one selected from the one or more organic layers comprises a material for an organic electroluminescent device represented by Formula 1:

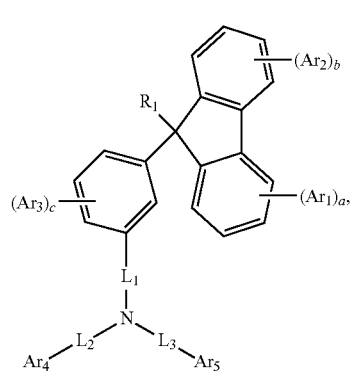

Formula 1 wherein,
$R_1$ is selected from a substituted or unsubstituted aryl group having 6 to 10 carbon atoms for forming a ring and an alkyl group having 1 to 20 carbon atoms;
$Ar_1$ to $Ar_5$ are each independently selected from a substituted or unsubstituted aryl group having 6 to 30 carbon atoms for forming a ring, a substituted or unsubstituted heteroaryl group having 5 to 30 carbon atoms for forming a ring, an alkyl group having 1 to 20 carbon atoms, a silyl group, a halogen atom, deuterium, and hydrogen;
at least one selected from $Ar_4$ and $Ar_5$ is a substituted or unsubstituted naphthyl group;
$L_1$ to $L_3$ are each independently selected from a single-bond and a substituted or unsubstituted arylene group having 6 to 12 carbon atoms for forming a ring;
$L_1$ is selected so that the quaternary carbon of the fluorenyl group and the nitrogen atom of the amine are at meta positions; and
a to c are each independently an integer selected from 0 to 4.

6. The organic electroluminescent device of claim 5, comprising:
an emission layer between the first electrode and the second electrode;
the material for an organic electroluminescent device being in at least one of the one or more organic layers between the first electrode and the emission layer.

7. The organic electroluminescent device of claim 5, wherein the organic layer comprising the material for an organic electroluminescent device is at least one selected from a hole injection layer and a hole transport layer.

8. The organic electroluminescent device of claim 5, wherein $R_1$ is selected from a substituted or unsubstituted phenyl group and a substituted or unsubstituted naphthyl group.

9. The organic electroluminescent device of claim 5, wherein at least one selected from $L_1$ to $L_3$ is a phenylene group.

10. The organic electroluminescent device of claim 5, wherein the material for an organic electroluminescent device represented by Formula 1 is further represented by at least one selected from Compounds 1 to 60:

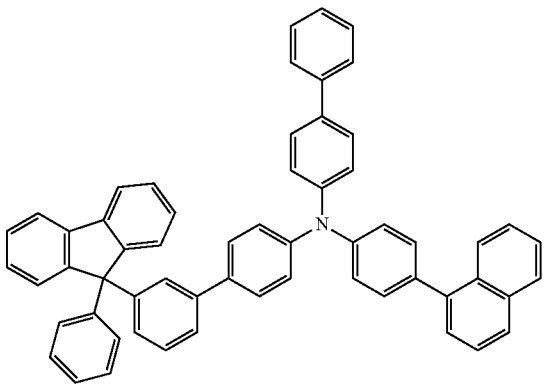

1

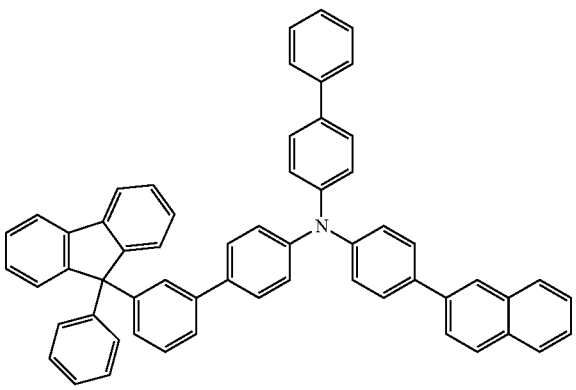

2

-continued

9
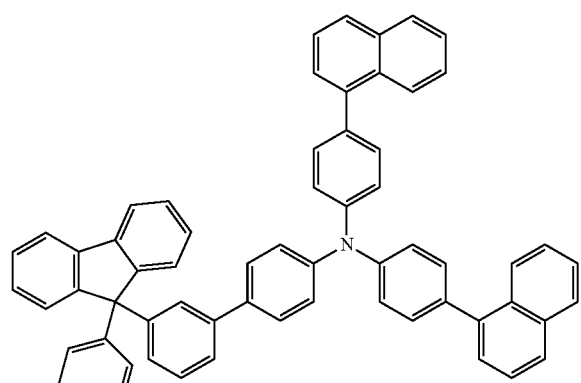
10
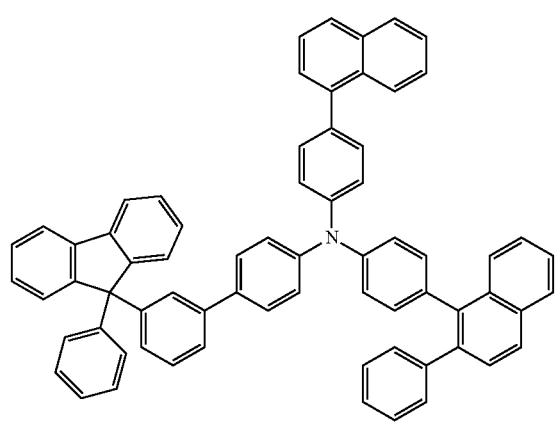
11
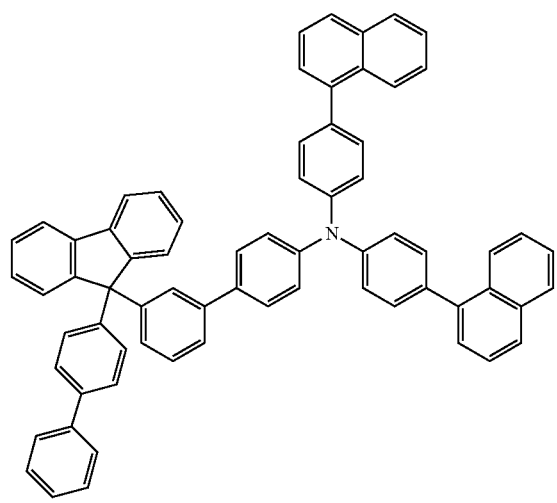
12
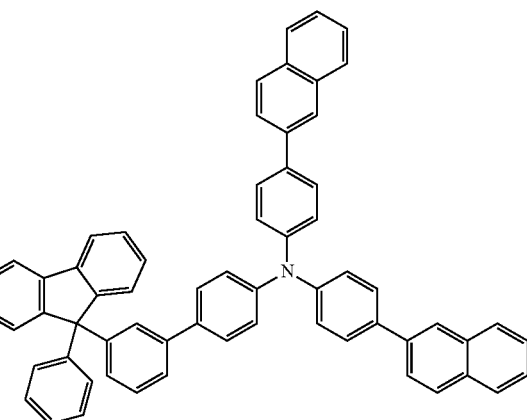
13
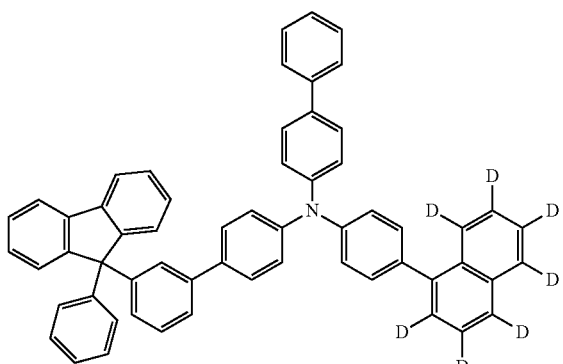
14
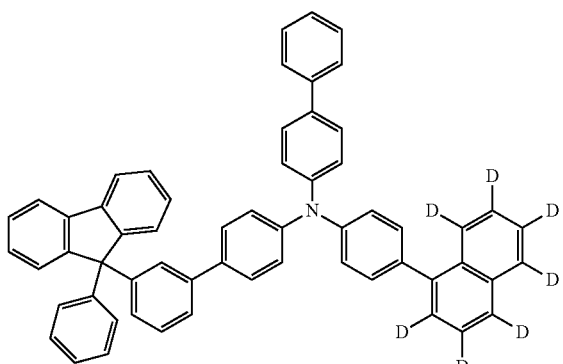

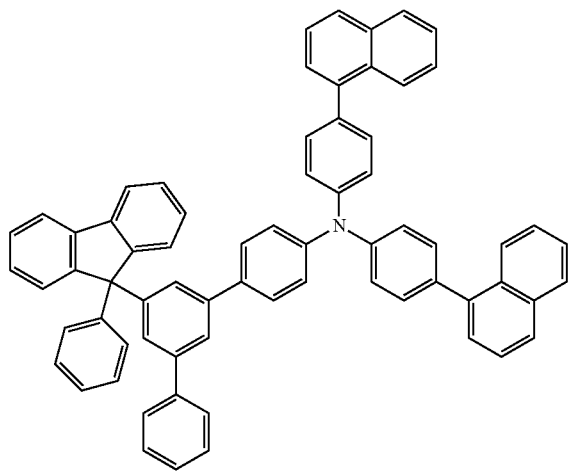
15
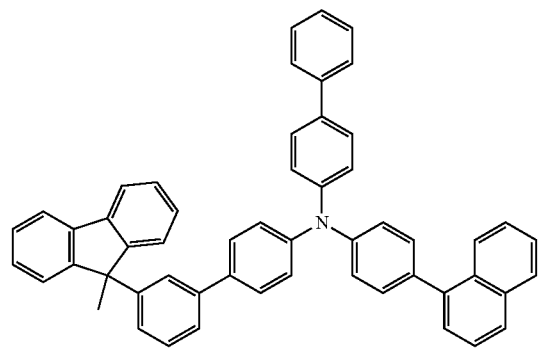
16
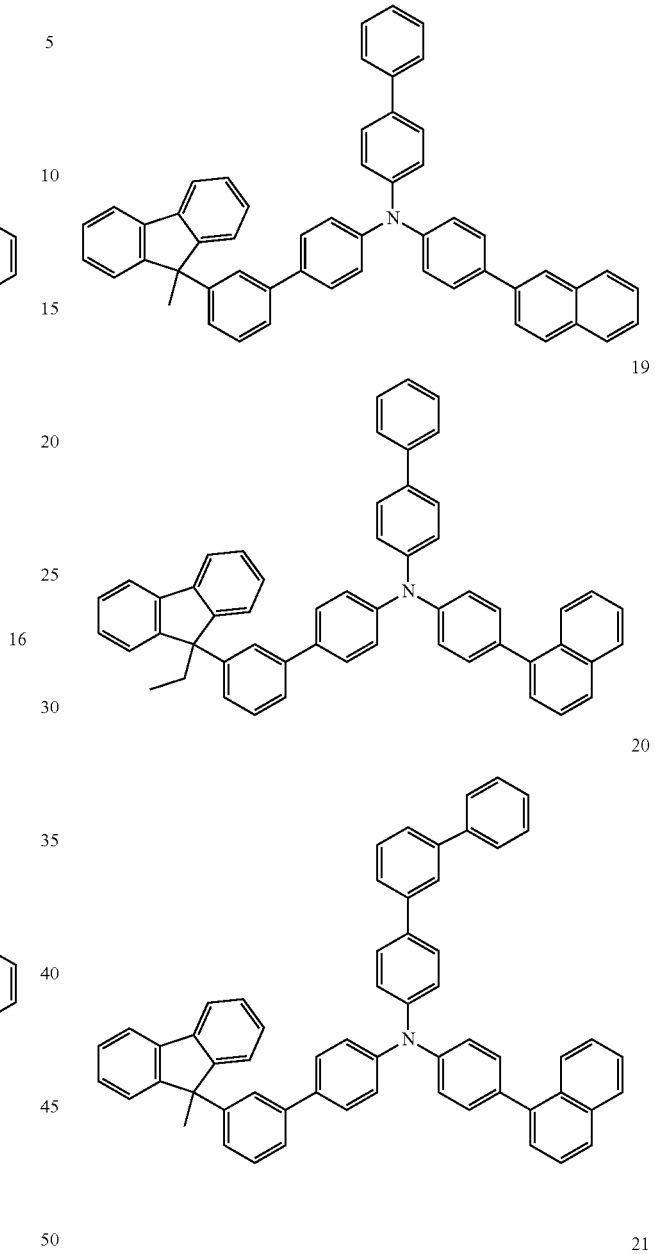
17
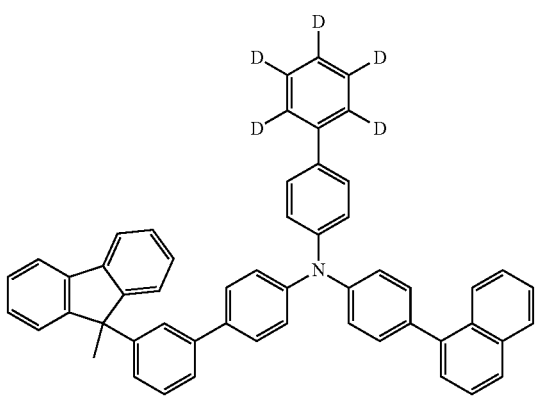

22
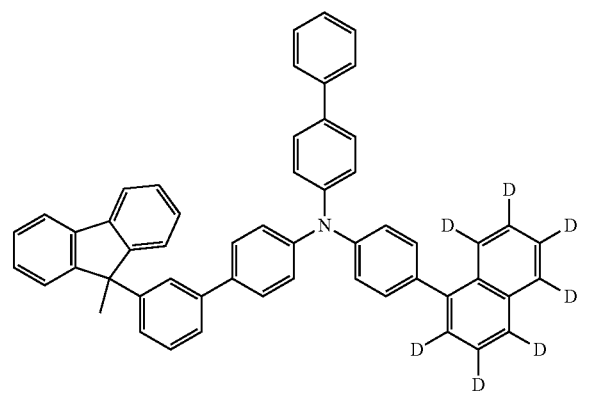
23
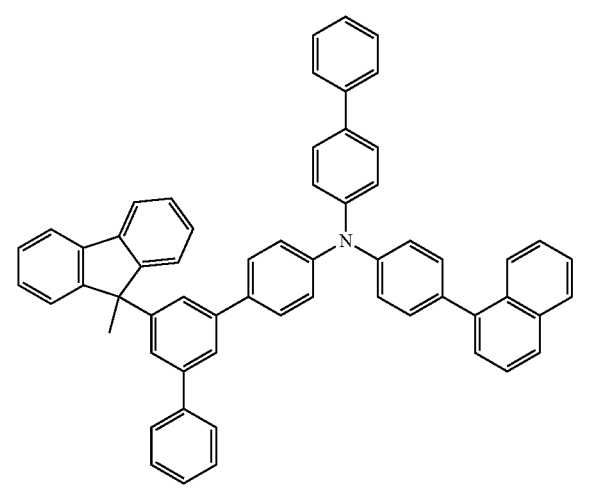
24
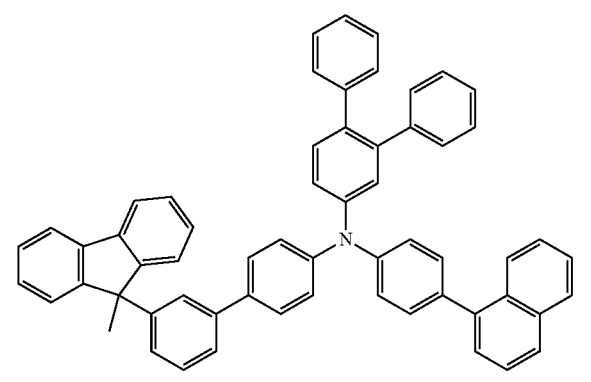
25
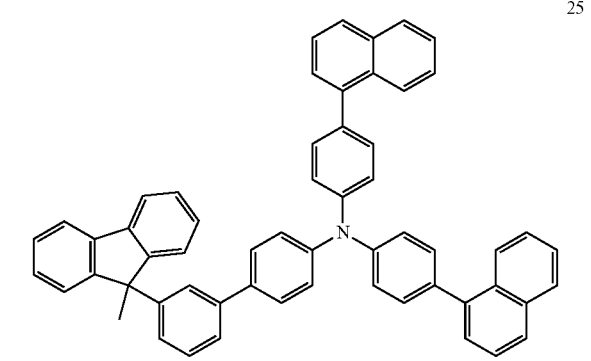
26
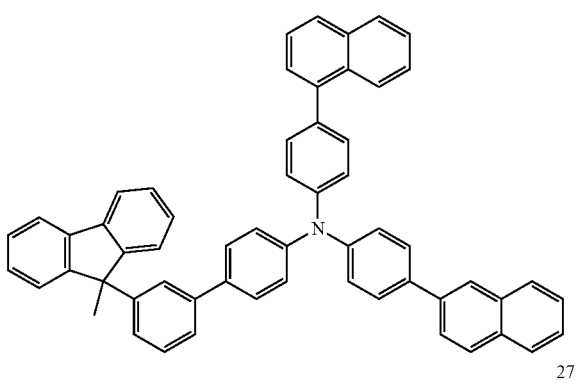
27
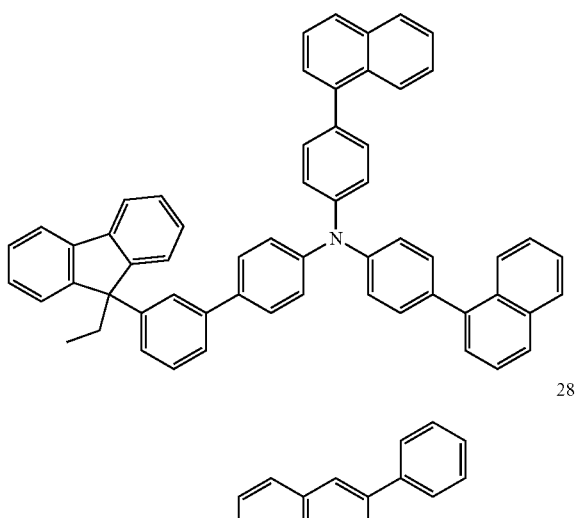
28
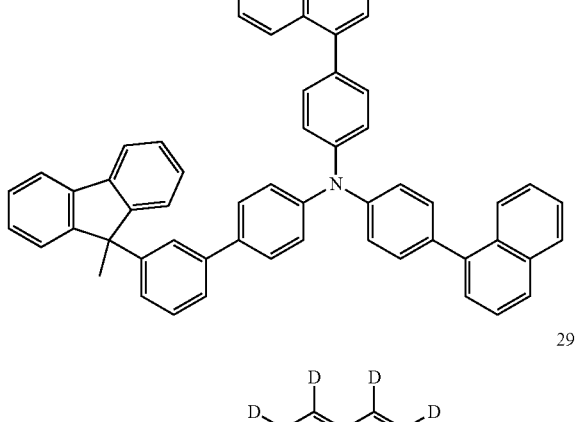
29
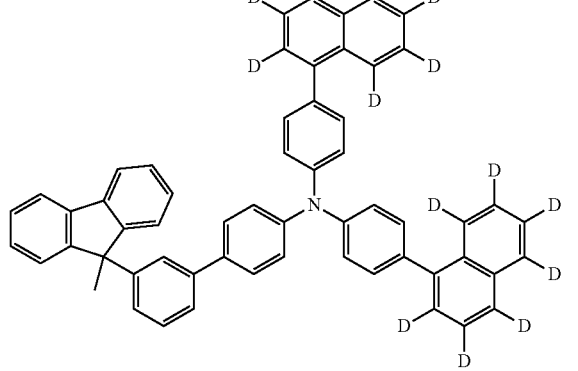

71
-continued
30
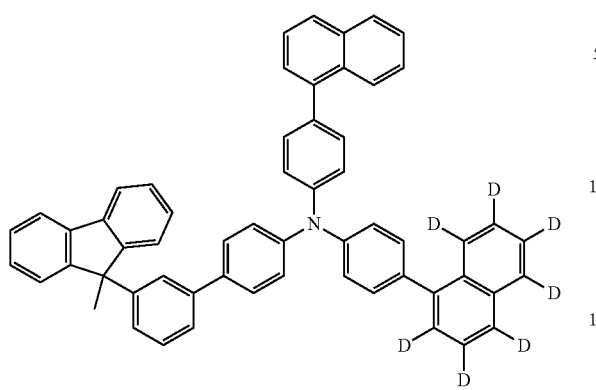
31
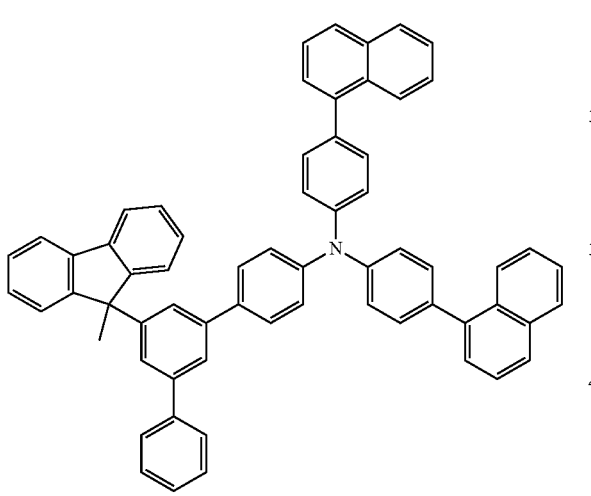
32
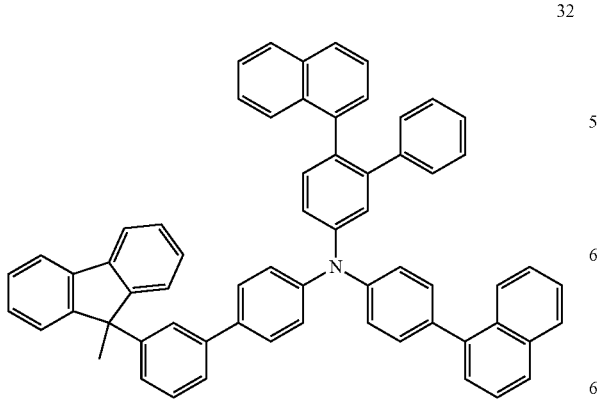
72
-continued
33
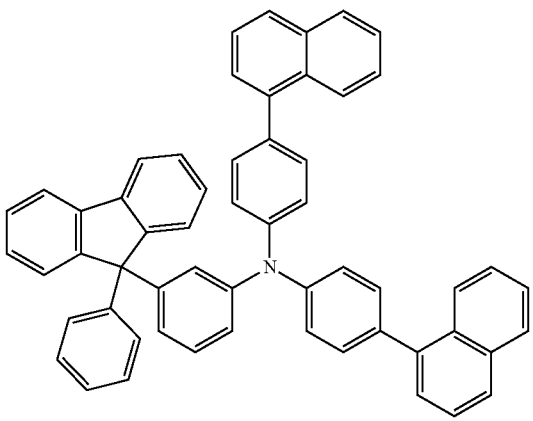
34
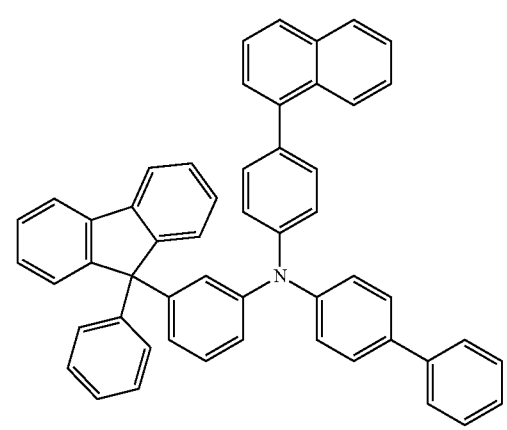
36
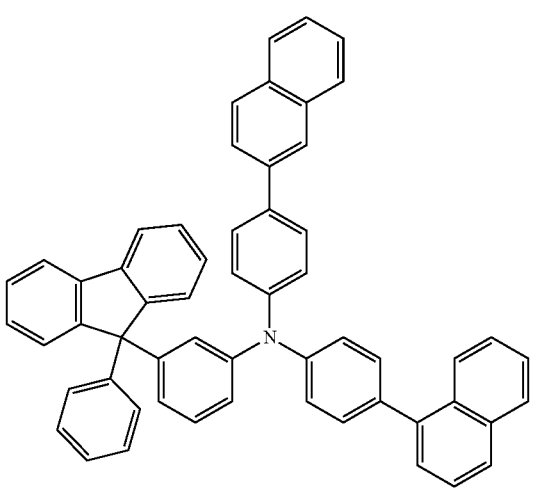

37
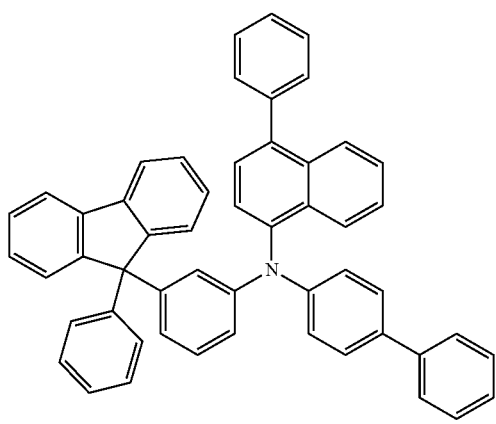
38
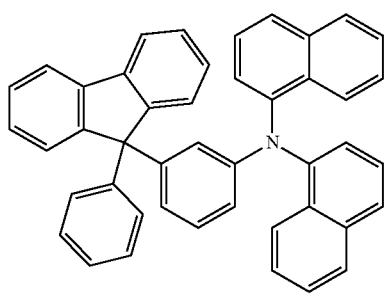
39
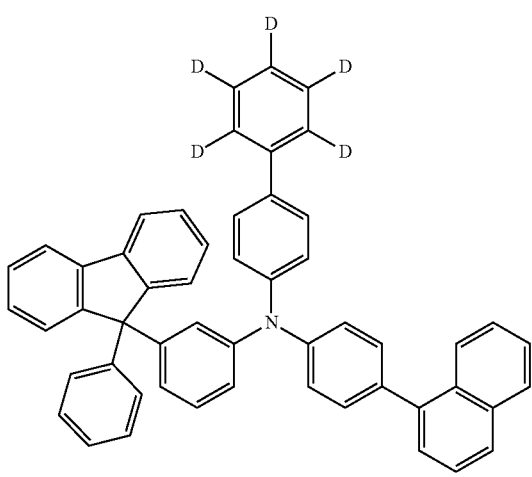
40
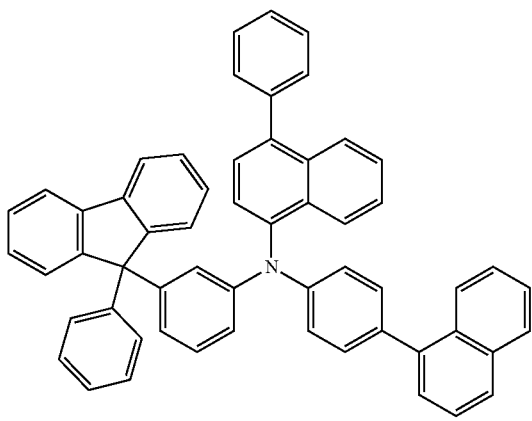
41
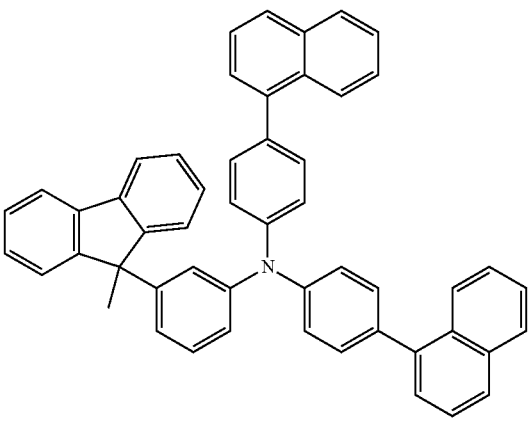
42
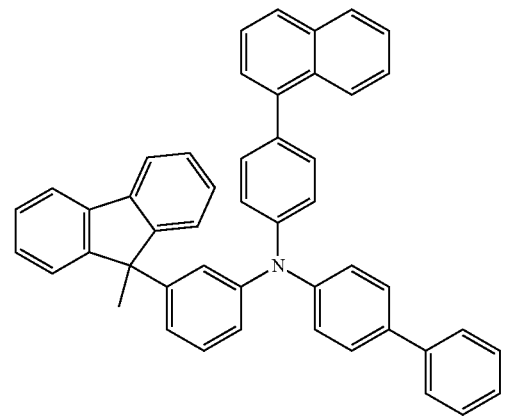
44
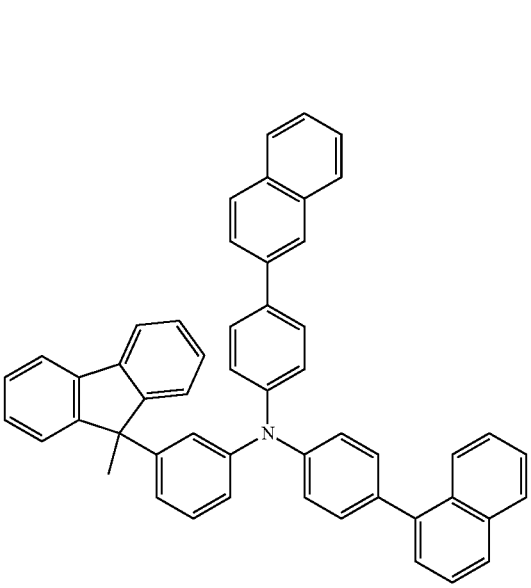

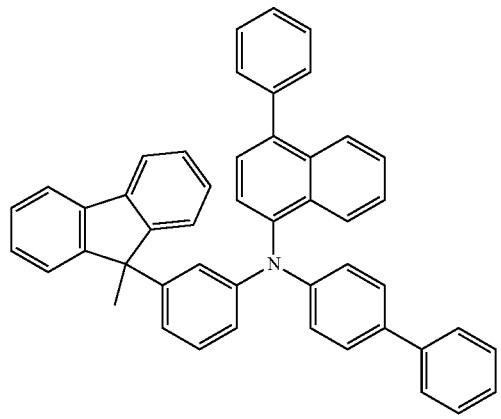
45
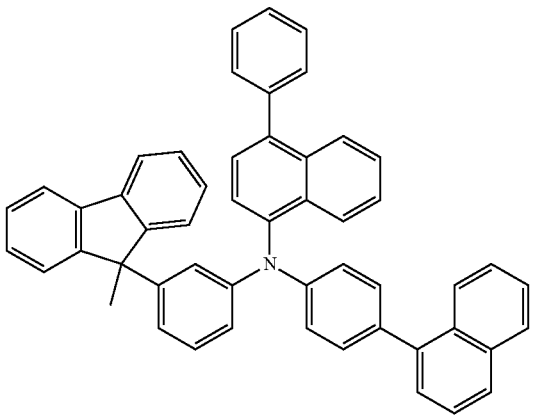
48
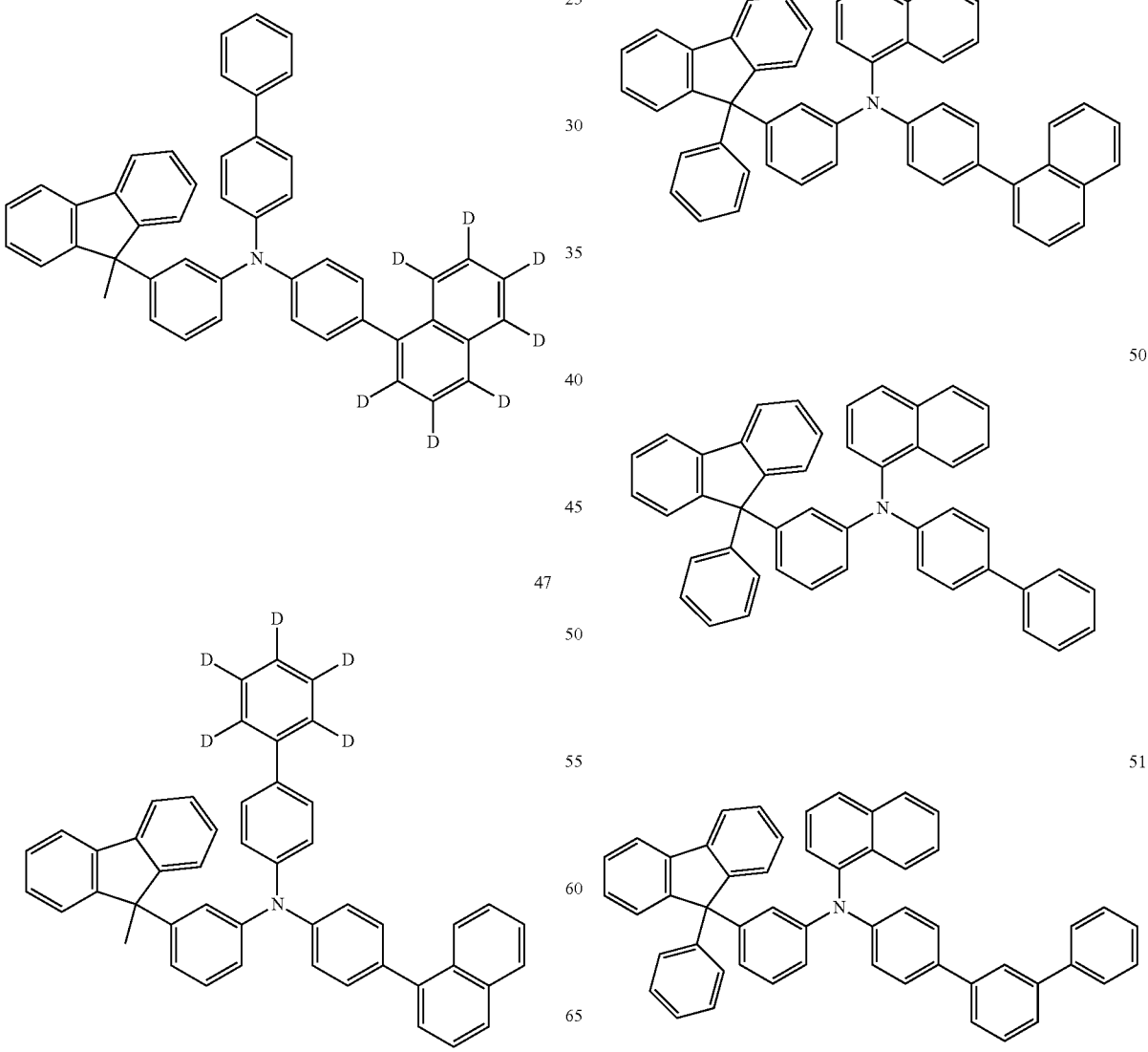

52
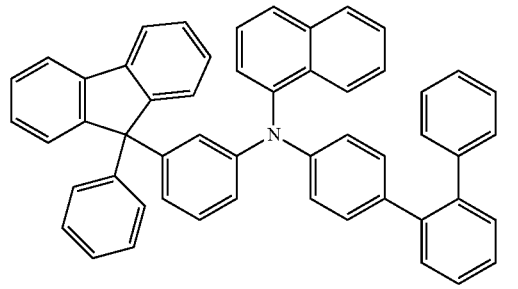
53
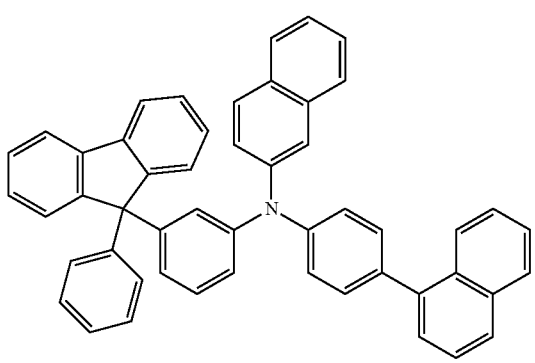
54
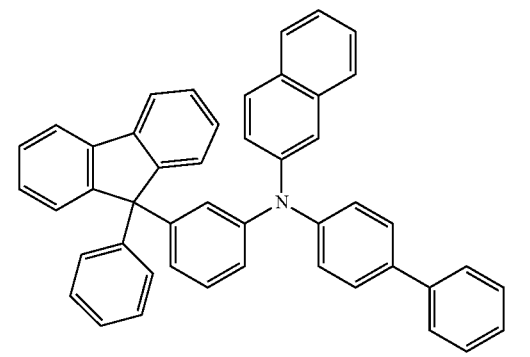
55
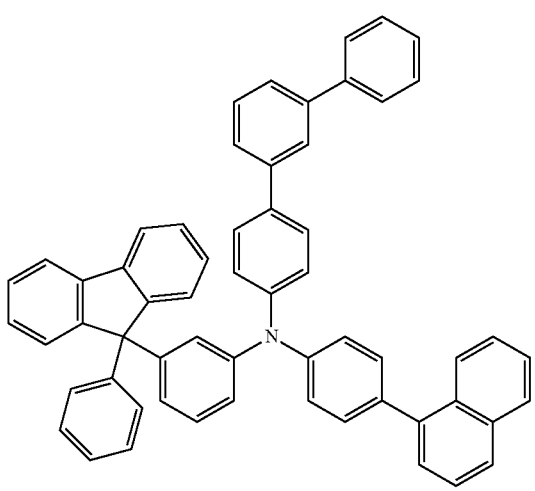
56
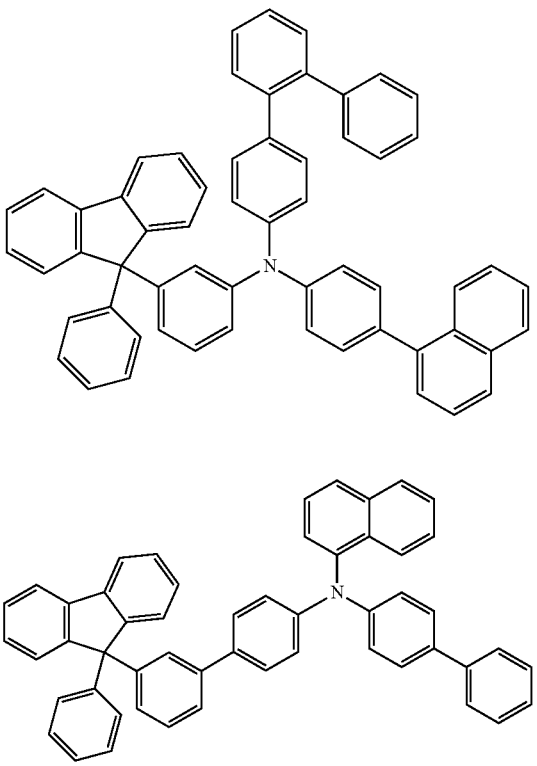
57
58
59
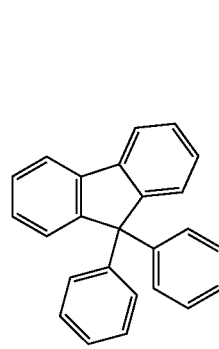

-continued
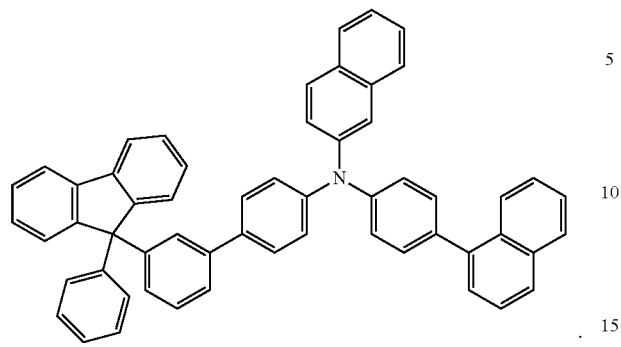
* * * * *